(12) United States Patent
Ochsner et al.

(10) Patent No.: US 10,538,771 B2
(45) Date of Patent: Jan. 21, 2020

(54) COMPOSITIONS AND METHODS FOR DETECTING MICROORGANISMS

(71) Applicant: SomaLogic, Inc., Boulder, CO (US)

(72) Inventors: Urs A. Ochsner, Boulder, CO (US); Nebojsa Janjic, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 16/118,596

(22) Filed: Aug. 31, 2018

(65) Prior Publication Data
US 2018/0371462 A1    Dec. 27, 2018

Related U.S. Application Data

(62) Division of application No. 15/112,739, filed as application No. PCT/US2015/015979 on Feb. 14, 2015, now Pat. No. 10,093,933.

(60) Provisional application No. 61/940,955, filed on Feb. 18, 2014, provisional application No. 61/947,627, filed on Mar. 4, 2014.

(51) Int. Cl.
| | |
|---|---|
| *C07H 21/02* | (2006.01) |
| *C07H 21/04* | (2006.01) |
| *C12N 15/115* | (2010.01) |
| *G01N 33/53* | (2006.01) |
| *G01N 33/569* | (2006.01) |
| *C12N 15/10* | (2006.01) |
| *C12Q 1/14* | (2006.01) |

(52) U.S. Cl.
CPC ........ *C12N 15/115* (2013.01); *C12N 15/1048* (2013.01); *C12Q 1/14* (2013.01); *G01N 33/5308* (2013.01); *G01N 33/569* (2013.01); *C12N 2310/16* (2013.01); *G01N 2333/31* (2013.01)

(58) Field of Classification Search
CPC .............................. C12N 15/115; A61K 45/06
See application file for complete search history.

(56) References Cited

U.S. PATENT DOCUMENTS

| | | | |
|---|---|---|---|
| 5,270,163 | A | 12/1993 | Gold et al. |
| 5,580,972 | A | 12/1996 | Tu |
| 5,582,981 | A | 12/1996 | Toole et al. |
| 5,719,273 | A | 2/1998 | Tu et al. |
| 5,840,867 | A | 11/1998 | Toole et al. |
| 5,874,218 | A | 2/1999 | Drolet et al. |
| 5,945,527 | A | 8/1999 | Tu et al. |
| 7,855,054 | B2 | 12/2010 | Schneider et al. |
| 7,947,447 | B2 | 5/2011 | Zichi et al. |
| 9,382,533 | B2 | 7/2016 | Zichi et al. |
| 2003/0054360 | A1 | 3/2003 | Gold et al. |
| 2009/0004667 | A1 | 1/2009 | Zichi et al. |
| 2009/0042206 | A1 | 2/2009 | Schneider et al. |
| 2009/0203028 | A1 | 8/2009 | Yamamoto et al. |
| 2011/0136099 | A1 | 6/2011 | Schneider et al. |
| 2012/0021415 | A1* | 1/2012 | Sempere .............. C12Q 1/6841 435/6.11 |
| 2012/0231467 | A1 | 9/2012 | Ochsner et al. |
| 2012/0276547 | A1 | 11/2012 | Le et al. |
| 2015/0148237 | A1 | 5/2015 | Zichi et al. |
| 2016/0215013 | A1 | 7/2016 | Rohloff et al. |
| 2016/0348112 | A1 | 12/2016 | Ochsner et al. |

FOREIGN PATENT DOCUMENTS

| | | | | |
|---|---|---|---|---|
| CN | 101460847 | A | 6/2009 | |
| EP | 1260592 | A1 * | 5/2001 | ........... A61K 31/713 |
| WO | WO 2012/122540 | | 9/2012 | |
| WO | WO 2013/185078 | | 12/2013 | |
| WO | WO 2015/124315 | | 8/2015 | |

OTHER PUBLICATIONS

Balogh et al. (Nov. 2010) FASEB J. 24(11):4187-4195, "Selection and versatile application of virus-specific aptamers".
Bartel et al. (1991) Cell 67:529-536, "HIV-1 Rev Regulation Involves Recognition of Non-Watson-Crick Base Pairs in Viral RNA".
Baumstummler et al. (2014) Letters in Applied Microbiology 59(4):422-431 "Specific capture and detection of *Staphylococcus aureus* with high-affinity modified aptamers to cell surface components".
Cao et al. (2009) Nucleic Acids Research 1-8, doi:10.1093/nar/gkp489 "Combining use of a panel of ssDNA aptamers in the detection of *Staphylococcus aureus*".
Chung et al. (2005) Electrophoresis, 26(3), pp. 694-702. "Microaffinity purification of proteins based on photolytic elution: toward an efficient microbead affinity chromatography on a chip".
Cibiel et al. (2011) Pharmaceuticals 4(9):1216-1235 "Methods to Identify Aptamers against cell Surface Biomarkers".
DiDonato (2006) Dissertation, University of North Carolina, Raleigh [entire paper].
European Partial Search Report dated Apr. 23, 2018 in EP 18153515.4.
Extended European Search Report dated Jul. 17, 2017 in EP 15751799.6.
Gnanam et al. (2008) Transactions of the Royal Society of Tropical Medicine and Hygiene 102/S1, S55-S57, "Development of aptamers specific for potential diagnostic targets in Burkholderia pseudomallei".

(Continued)

*Primary Examiner* — Amy H Bowman
(74) *Attorney, Agent, or Firm* — Adsero IP

(57) ABSTRACT

Described herein are compositions and methods for detecting the presence or absence of a microorganism in a sample comprising contacting the sample with an aptamer capable of binding to a cell-surface protein of the microorganism to form a complex, contacting the mixture with a second aptamer capable of binding to the first cell-surface protein or a second cell-surface protein of the microorganism; and performing an assay to detect the second aptamer, wherein detecting the second aptamer indicates that the microorganism is present in the sample, and wherein not detecting the second aptamer indicates that the microorganism is absent from the sample.

4 Claims, 6 Drawing Sheets
Specification includes a Sequence Listing.

(56) References Cited

OTHER PUBLICATIONS

Gold et al. (Jan. 1, 1995) Harvey Lectures 91:47-57, "The SELEX Process: A Surprising Source of Therapeutic and Diagnostic Compounds".
IPRP issued Aug. 23, 2016 in PCT/US2015/015979.
ISR and Written Opinion dated Jul. 30, 2015 in PCT/US2015/015979.
Ochsner et al. (2013) Diagnostic Microbiology and Infectious Disease 76(3):278-285 "Detection of Clostridium difficiletoxins A, B and binary toxin with slow off-rate modified aptamers".
Vaught et al. (Mar. 2010) J.Am. Chem. Soc. ePub, 132(12):4141-4151:4142, "Expanding the Chemistry of DNA for In Vitro Selection".
Vaught, Jonathan David, Thesis Oct. 2008, "Enhancing the Functionality of Nucleic Acids".
Wang et al. (2000) RNA 6:571-583, "In vitro selection of novel RNA ligands that bind human cytomegalovirus and block viral infection".
Wochner et al. (2007) Expert Opin. Drug Discov. 2(9):1205-1224 "Characterisation of aptamers for therapeutic studies".
Zelada-Guillen et al. (2009) Angew. Chem. In. Ed. 48:1-4, "Immediate Detection of Living Bacteria at Ultralow Concentrations Using a Carbon Nanotube Based Potentiometric Aptasensor".
Zichi et al. (Mar. 7, 2008) Current Opinion in Chemical Biology 12(1):78-85, "Proteomics and diagnostics: Let's Get Specific, again".

\* cited by examiner

SEQUENCE LISTING

<160> NUMBER OF SEQ ID NOS: 15

<210> SEQ ID NO 1
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (18)..(19)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (21)..(21)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (35)..(35)
<223> OTHER INFORMATION: 5-[N-(1-naphthylmethyl)carboxyamide]-2'-
      deoxyuridine

<400> SEQUENCE: 1
ccggcnncgg gnaccnanna ncggnnnagc ccagncataa                              40

<210> SEQ ID NO 2
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (6)..(7)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (18)..(19)

<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (21)..(21)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (35)..(35)
<223> OTHER INFORMATION: 5-[N-(1-naphthylmethyl)carboxyamide]-2'-
      deoxyuridine

<400> SEQUENCE: 2
ncggcnncgg gnaccnanna ncggnnnagc ccagncagaa                              40

<210> SEQ ID NO 3
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (18)..(19)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (21)..(21)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (35)..(35)
<223> OTHER INFORMATION: 5-[N-(1-naphthylmethyl)carboxyamide]-2'-
      deoxyuridine

<400> SEQUENCE: 3
gcggcnncgg gnaccnanna ncggnnnagc ccagncaaaa                              40

<210> SEQ ID NO 4
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)

<220> FEATURE:
<221> NAME/KEY: misc_feature
<222> LOCATION: (6)..(7)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (18)..(19)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (21)..(21)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (35)..(35)
<223> OTHER INFORMATION: 5-[N-(1-naphthylmethyl)carboxyamide]-2'-
deoxyuridine

<400> SEQUENCE: 4
gnggcnncgg gnaccnanna ncggnnnagc ccagncagaa                40

<210> SEQ ID NO 5
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (18)..(19)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (21)..(21)
<223> OTHER INFORMATION: 5-[N-(1-naphthylmethyl)carboxyamide]-2'-
deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
deoxyuridine

```
<220> FEATURE:
<221> NAME/KEY: misc_feature
<222> LOCATION: (33)..(33)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (35)..(35)
<223> OTHER INFORMATION: 5-[N-(1-naphthylmethyl)carboxyamide]-2'-
      deoxyuridine

<400> SEQUENCE: 5
gcggcnncgg gnaccnanna ncggnnnagc ccngncagga                        40

<210> SEQ ID NO 6
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (5)..(5)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (14)..(15)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (20)..(20)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (24)..(24)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (26)..(27)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (29)..(30)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (33)..(35)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (43)..(43)
<223> OTHER INFORMATION: 5-[N-(1-naphthylmethyl)carboxyamide]-2'-
      deoxyuridine

<400> SEQUENCE: 6
gngancgagc ggcnncgggn accnannann ggnnnagccc agncagaa              48

<210> SEQ ID NO 7
<211> LENGTH: 40
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (6)..(7)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (18)..(19)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (21)..(21)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (35)..(35)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (37)..(37)
<223> OTHER INFORMATION: 5-[N-(1-naphthylmethyl)carboxyamide]-2'-
      deoxyuridine

<400> SEQUENCE: 7
ncggcnncgg gnaccnanna ncggnnnagc ccagncngaa                              40

<210> SEQ ID NO 8
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (12)..(12)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (16)..(16)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (18)..(19)
<223> OTHER INFORMATION: 5-[N-(1-naphthylmethyl)carboxyamide]-2'-
      deoxyuridine
<220> FEATURE:
<221> NAME/KEY: misc_feature
```

```
<222> LOCATION: (21)..(21)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (25)..(27)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (34)..(34)
<223> OTHER INFORMATION: 5-[N-(1-naphthylmethyl)carboxyamide]-2'-
      deoxyuridine

<400> SEQUENCE: 8
acggcnncgg gnaccnanna ncggnnnagc cagncagaa                              39

<210> SEQ ID NO 9
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (10)..(10)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (14)..(14)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (16)..(17)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (19)..(19)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (22)..(24)
<223> OTHER INFORMATION: 5-[N-(1-naphthylmethyl)carboxyamide]-2'-
      deoxyuridine
<220> FEATURE:
<221> NAME/KEY: misc_feature
<222> LOCATION: (30)..(30)
<223> OTHER INFORMATION: 5-[N-(1-naphthylmethyl)carboxyamide]-2'-
      deoxyuridine

<400> SEQUENCE: 9
ggcnncgggn accnannang gnnnagccgn c                                      31

<210> SEQ ID NO 10
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
```

```
<223> OTHER INFORMATION: 5-(N-benzylcarboxyamide)-2'-deoxyuridine
<220> FEATURE:
<221> NAME/KEY: misc_feature
<222> LOCATION: (7)..(8)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (27)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)
<223> OTHER INFORMATION: 5-(N-benzylcarboxyamide)-2'-deoxyuridine
<220> FEATURE:
<221> NAME/KEY: misc_feature
<222> LOCATION: (32)..(36)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 10
ancnggnnca aagngacgan ngggcancng gnnnnnaagn                    40

<210> SEQ ID NO 11
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (7)..(8)
<223> OTHER INFORMATION: 5-(N-benzylcarboxyamide)-2'-deoxyuridine
<220> FEATURE:
<221> NAME/KEY: misc_feature
<222> LOCATION: (10)..(10)
<223> OTHER INFORMATION: 5-(N-benzylcarboxyamide)-2'-deoxyuridine
<220> FEATURE:
<221> NAME/KEY: misc_feature
<222> LOCATION: (14)..(15)
<223> OTHER INFORMATION: 5-(N-benzylcarboxyamide)-2'-deoxyuridine
<220> FEATURE:
<221> NAME/KEY: misc_feature
<222> LOCATION: (18)..(19)
<223> OTHER INFORMATION: 5-(N-benzylcarboxyamide)-2'-deoxyuridine
<220> FEATURE:
<221> NAME/KEY: misc_feature
<222> LOCATION: (24)..(24)
<223> OTHER INFORMATION: 5-(N-benzylcarboxyamide)-2'-deoxyuridine
<220> FEATURE:
<221> NAME/KEY: misc_feature
<222> LOCATION: (27)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)
<223> OTHER INFORMATION: 5-(N-benzylcarboxyamide)-2'-deoxyuridine
<220> FEATURE:
<221> NAME/KEY: misc_feature
```

<222> LOCATION: (32)..(36)
<223> OTHER INFORMATION: 5-(N-benzylcarboxyamide)-2'-deoxyuridine

<400> SEQUENCE: 11
ancnggnncn aagnnacnng gcgnaancng gnnnnnaaga                            40

<210> SEQ ID NO 12
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (7)..(8)
<223> OTHER INFORMATION: 5-(N-benzylcarboxyamide)-2'-deoxyuridine
<220> FEATURE:
<221> NAME/KEY: misc_feature
<222> LOCATION: (14)..(14)
<223> OTHER INFORMATION: 5-(N-benzylcarboxyamide)-2'-deoxyuridine
<220> FEATURE:
<221> NAME/KEY: misc_feature
<222> LOCATION: (20)..(21)
<223> OTHER INFORMATION: 5-(N-benzylcarboxyamide)-2'-deoxyuridine
<220> FEATURE:
<221> NAME/KEY: misc_feature
<222> LOCATION: (27)..(27)
<223> OTHER INFORMATION: 5-(N-benzylcarboxyamide)-2'-deoxyuridine
<220> FEATURE:
<221> NAME/KEY: misc_feature
<222> LOCATION: (29)..(29)
<223> OTHER INFORMATION: 5-(N-benzylcarboxyamide)-2'-deoxyuridine
<220> FEATURE:
<221> NAME/KEY: misc_feature
<222> LOCATION: (32)..(36)
<223> OTHER INFORMATION: 5-(N-benzylcarboxyamide)-2'-deoxyuridine
<220> FEATURE:
<221> NAME/KEY: misc_feature
<222> LOCATION: (40)..(40)
<223> OTHER INFORMATION: 5-(N-benzylcarboxyamide)-2'-deoxyuridine

<400> SEQUENCE: 12
ancnggnnca aagnggcgan ngggcancng gnnnnnaagn                            40

<210> SEQ ID NO 13
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 5-(N-benzylcarboxyamide)-2'-deoxyuridine
<220> FEATURE:
<221> NAME/KEY: misc_feature
<222> LOCATION: (4)..(4)
<223> OTHER INFORMATION: 5-(N-benzylcarboxyamide)-2'-deoxyuridine
<220> FEATURE:
<221> NAME/KEY: misc_feature
<222> LOCATION: (7)..(8)
<223> OTHER INFORMATION: 5-(N-benzylcarboxyamide)-2'-deoxyuridine
<220> FEATURE:
<221> NAME/KEY: misc_feature
<222> LOCATION: (11)..(11)
<223> OTHER INFORMATION: 5-(N-benzylcarboxyamide)-2'-deoxyuridine
<220> FEATURE:

<220> FEATURE:
<221> NAME/KEY: misc_feature
<222> LOCATION: (13)..(13)
<223> OTHER INFORMATION: 5-(N-benzylcarboxyamide)-2'-deoxyuridine
<220> FEATURE:
<221> NAME/KEY: misc_feature
<222> LOCATION: (16)..(20)
<223> OTHER INFORMATION: 5-(N-benzylcarboxyamide)-2'-deoxyuridine

<400> SEQUENCE: 13
ancnggnnca ncnggnnnnn aag                                               23

<210> SEQ ID NO 14
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: C-5 modified pyrimidine
<220> FEATURE:
<221> NAME/KEY: misc_feature
<222> LOCATION: (10)..(10)
<223> OTHER INFORMATION: C-5 modified pyrimidine
<220> FEATURE:
<221> NAME/KEY: misc_feature
<222> LOCATION: (14)..(14)
<223> OTHER INFORMATION: C-5 modified pyrimidine
<220> FEATURE:
<221> NAME/KEY: misc_feature
<222> LOCATION: (16)..(17)
<223> OTHER INFORMATION: C-5 modified pyrimidine
<220> FEATURE:
<221> NAME/KEY: misc_feature
<222> LOCATION: (19)..(19)
<223> OTHER INFORMATION: C-5 modified pyrimidine
<220> FEATURE:
<221> NAME/KEY: misc_feature
<222> LOCATION: (20)..(20)
<223> OTHER INFORMATION: unmodified or modified nucleotide
<220> FEATURE:
<221> NAME/KEY: misc_feature
<222> LOCATION: (23)..(25)
<223> OTHER INFORMATION: C-5 modified pyrimidine
<220> FEATURE:
<221> NAME/KEY: misc_feature
<222> LOCATION: (30)..(31)
<223> OTHER INFORMATION: unmodified or modified nucleotide, and may be
    absent
<220> FEATURE:
<221> NAME/KEY: misc_feature
<222> LOCATION: (33)..(33)
<223> OTHER INFORMATION: C-5 modified pyrimidine

<400> SEQUENCE: 14
ggcnncgggn accnannann ggnnnagccn ngnc                                   34

<210> SEQ ID NO 15
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: C-5 modified pyrimidine
<220> FEATURE:
<221> NAME/KEY: misc_feature
<222> LOCATION: (4)..(4)
<223> OTHER INFORMATION: C-5 modified pyrimidine
<220> FEATURE:
<221> NAME/KEY: misc_feature
<222> LOCATION: (7)..(8)

```
<223> OTHER INFORMATION: C-5 modified pyrimidine
<220> FEATURE:
<221> NAME/KEY: misc_feature
<222> LOCATION: (10)..(39)
<223> OTHER INFORMATION: unmodified or modified nucleotide and may be
      absent
<220> FEATURE:
<221> NAME/KEY: misc_feature
<222> LOCATION: (41)..(41)
<223> OTHER INFORMATION: C-5 modified pyrimidine
<220> FEATURE:
<221> NAME/KEY: misc_feature
<222> LOCATION: (43)..(43)
<223> OTHER INFORMATION: C-5 modified pyrimidine
<220> FEATURE:
<221> NAME/KEY: misc_feature
<222> LOCATION: (46)..(50)
<223> OTHER INFORMATION: C-5 modified pyrimidine

<400> SEQUENCE: 15
ancnggnncn nnnnnnnnnn nnnnnnnnnn nnnnnnnnna ncnggnnnnn aag              53
```

COMPOSITIONS AND METHODS FOR DETECTING MICROORGANISMS

RELATED APPLICATIONS

This application is a divisional of U.S. application Ser. No. 15/112,739, filed Jul. 20, 2016. U.S. application Ser. No. 15/112,739 is a 35 U.S.C. § 371 national phase application of International Application Serial No. PCT/US2015/015979, filed Feb. 14, 2015. International Application Serial No. PCT/US2015/015979 claims priority to U.S. Provisional Application Ser. No. 61/940,955, filed Feb. 18, 2014, and U.S. Provisional Application Ser. No. 61/947,627, filed Mar. 4, 2014, each of which is incorporated herein by reference in its entirety.

Incorporated by reference herein in its entirety is the Sequence Listing entitled "Sequence_Listing_ST25", created Feb. 13, 2015 size of 16 kilobytes.

FIELD

The present disclosure relates generally to composition and methods for detecting for the presence of a microorganism in a sample. More specifically, the disclosure relates to nucleic acid aptamers capable of binding microorganism protein, and methods for the capture and detection of a microorganism with nucleic acid aptamers in a sample.

BACKGROUND

The contamination of food and water poses a major health risk in both developed countries and third world countries, and is thought to be responsible for millions of human deaths and illnesses annually. Moreover, contamination to food and water also threatens animal health, including livestock and aquatic ecosystems.

Generally, these illnesses are caused by microorganism contamination, such as bacteria, parasites or viruses. With respect to food production, the complexity and the number of parties involved provide an abundant number of opportunities for unintentional contamination, and the potential and unfortunate interplay of terrorism and food supply. Surface and ground water generally become contaminated by pets, livestock or wild animal defecating in or near a water source, while run-off from landfills, septic fields, sewers and agricultural lands also contribute to water contamination. Irrespective of the type and source of contamination, it can be difficult for individuals to determine if food or water is contaminated because it may appear and taste fine, but still cause illness and ultimately death. Thus, monitoring for microbial contamination of food, water, non-sterile products, or the environment is critical to public health on a global scale Therefore, there continues to be a need for alternative compositions and methods for improved, cost-effective and efficient monitoring for microbial contamination in both food and water. The present disclosure meets such needs by providing novel aptamer reagents with high specificity and affinity for cell surface epitopes on a microorganism for the capture and enrichment of a microorganism present at low cell densities and for the direct detection (e.g., by qPCR or fluorescent staining) without the need for culture or cell lysis.

SUMMARY

The present disclosure describes the generation of novel slow off-rate modified aptamer (SOMAmer) reagents to several *Staphylococcus aureus* cell surface-associated proteins via SELEX with multiple modified DNA libraries using purified recombinant or native proteins. High-affinity binding agents with sub-nanomolar K's were obtained for staphylococcal protein A (SpA), clumping factors (ClfA, ClfB), fibronectin-binding proteins (FnbA, FnbB) and iron-regulated surface determinants (Isd). Several aptamers specifically bound to *S. aureus* cells from all strains that were tested, but not to other staphylococci or other bacteria. SpA and ClfA aptamers proved useful for the selective capture and enrichment of *S. aureus* cells from low cell-density matrices, as shown by culture and PCR, leading to improved limits of detection and efficient removal of PCR inhibitors. Detection of *S. aureus* cells was enhanced by several orders of magnitude when the bacterial cell surface was coated with aptamers followed by qPCR of the aptamers compared to genomic PCR.

The present disclosure describes a method for detecting the presence or absence of a microorganism in a sample comprising: a) contacting the sample with a first aptamer to form a mixture, wherein the first aptamer is capable of binding to a first cell-surface protein of the microorganism to form a complex and comprises a first tag, wherein the first tag is capable of binding to a solid support; b) contacting the mixture with the solid support under conditions that permit the first tag to bind to the solid support; c) washing the solid support to enrich the mixture for the complex and/or washing the solid support to substantially remove unbound material; c) contacting the mixture with a second aptamer, wherein the second aptamer is capable of binding to the first cell-surface protein or a second cell-surface protein of the microorganism; and d) performing an assay to detect the second aptamer, wherein detecting the second aptamer indicates that the microorganism is present in the sample, and wherein not detecting the second aptamer indicates that the microorganism is absent from the sample.

The present disclosure further provides for a method for detecting the presence or absence of a microorganism in a sample comprising:

a) contacting the sample with a solid support, wherein a first aptamer is bound to the solid support via a first tag, and wherein the first aptamer is capable of binding to a first cell-surface protein of the microorganism to form a complex; b) washing the solid support to enrich the mixture for the complex and/or washing the solid support to substantially remove unbound material; c) contacting the mixture with a second aptamer, wherein the second aptamer is capable of binding to the first cell-surface protein or a second cell-surface protein of the microorganism and comprises a second tag; and d) performing an assay to detect the second aptamer, wherein detecting the second aptamer indicates that the microorganism is present in the sample, and wherein not detecting the second aptamer indicates that the microorganism is absent from the sample.

In another aspect, the at least one of the first aptamer and the second aptamer further comprise at least one C-5 modified pyrimidine. In a related aspect, the C-5 modified pyrimidine is selected from the group consisting of 5-(N-benzylcarboxyamide)-2'-deoxycytidine (BndC); 5-(N-2-phen- yl-ethylcarboxyamide)-2'-deoxycytidine (PEdC); 5-(N-3-phenylpropylcarboxyamide)-2'-deoxycytidine (PPdC); 5-(N-1-naphthylmethylcarboxyamide)-2'-deoxycytidine (NapdC); 5-(N-2-naphthylmethylcarboxyamide)-2'-deoxycytidine (2 NapdC); 5-(N-1-naphthyl-2-ethylcarboxyamide)-2'-deoxycytidine (NEdC); 5-(N-2-naphthyl-2-ethylcarboxyamide)-2'-deoxycytidine (2NEdC); 5-(N-benzylcarboxyamide)-2'-deoxyuridine (BndU); 5-(N-isobutylcarboxyamide)-2'- deoxyuridine (iBudU); 5-(N-tryptaminocarboxyamide)-2'-deoxyuridine (TrpdU); 5-(N-[1-(3-trimethylamonium) propyl]carboxyamide)-2'-deoxyuridine chloride and 5-(N-naphthylmethylcarboxyamide)-2'-deoxyuridine (NapdU).

In another aspect, the second aptamer is amplifiable. In a related aspect, the second aptamer is a template for enzymatic amplifications (e.g. by PCR or qPCR). In yet another related aspect, the second aptamer is amplified by PCR primers that are capable of hybridizing with the second aptamer or one or more regions of the second aptamer.

In another aspect, the second aptamer comprises a second tag, wherein the second tag is selected from the group consisting of a dye, a quantum dot, a radiolabel, PCR primer sites, an electrochemical functional group, and an enzyme plus a detectable enzyme substrate.

In another aspect, the first tag is selected from the group consisting of a polynucleotide, a polypeptide, a peptide nucleic acid, a locked nucleic acid, an oligosaccharide, a polysaccharide, an antibody, an affibody, an antibody mimic, a cell receptor, a ligand, a lipid, biotin, polyhistidine, or any fragment or derivative of these structures.

In another aspect, solid support is selected from the group consisting of a bead and a substrate. In a related aspect, the bead is selected from the group consisting of a polymer bead, an agarose bead, a polystyrene bead, an acrylamide bead, a solid core bead, a porous bead, a paramagnetic bead, glass bead, microbead, and controlled pore bead. In yet another related aspect, the substrate is selected from the group consisting of a microtiter well, a cyclo-olefin copolymer substrate, a membrane, a plastic substrate, nylon, a Langmuir-Blodgett film, glass, a germanium substrate, a silicon substrate, a silicon wafer chip, a flow through chip, a nanoparticle, a polytetrafluoroethylene substrate, a polystyrene substrate, a gallium arsenide substrate, a gold substrate, and a silver substrate.

In another aspect, the assay is selected from the group including but not limited to PCR, qPCR, mass spectroscopy, sequencing hybridization and the like. In a related aspect, the assay is selected from the group consisting of PCR and qPCR.

In another aspect, the microorganism is selected from the group including, but not limited to a bacterial cell, parasite and virus.

In another aspect, the microorganism is a bacterial cell. In a related aspect, the bacterial cell is pathogenic. In yet another related aspect, the bacterial cell is a *Staphylococcus* cell. In another related aspect, the bacterial cell is a *Staphylococcus aureus* cell.

In another aspect, the first cell-surface protein and the second cell-surface protein are the same protein or a different protein.

In another aspect, the first cell-surface protein is a bacterial cell-surface protein.

In another aspect, the second cell-surface protein is a bacterial cell-surface protein.

In another aspect, the first cell-surface protein is selected from the group consisting of SPA, ClfA, ClfB, FnbA, FnbB, IsdA, IsdB, IsdC, IsdH and SasD. In a related aspect, the first cell-surface protein is selected from the group consisting of SPA and ClfA.

In another aspect, the second cell-surface protein is selected from the group consisting of SPA, ClfA, ClfB, FnbA, FnbB, IsdA, IsdB, IsdC, IsdH and SasD. In a related aspect, the second cell-surface protein is selected from the group consisting of SPA and ClfA.

In another aspect, the first aptamer comprises a nucleic acid molecule having the sequence of GGCWWCGGG-WACCWAWWAWNGGWWWAGCC(N)$_n$GWC (SEQ ID NO: 14), wherein W is independently, for each occurrence, a C-5 modified pyrimidine, N is any unmodified or modified nucleotide, and n is 0, 1, 2, 3, 4 or 5. In a related aspect, n is 2. In a related aspect, the first aptamer is at least about 32, 33, 34, 35, 36, 37, 38, 39, 40, 41, 42, 43, 44, 45, 46, 47, 48, 49 or 50 nucleotides in length. In yet another related aspect, the first aptamer is at from about 32 to about 100 nucleotides in length (or 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the first aptamer comprises a nucleic acid molecule having the sequence of AWCWGGWWC(N)$_n$AWCWGGWWWWWAAG (SEQ ID NO: 15), wherein W is independently, for each occurrence, a C-5 modified pyrimidine, N is any unmodified or modified nucleotide, and n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In a related aspect, n is from 5 to 20 (or 5, 6, 7, 8, 9, 10, 11, 12, 13, 14, 15, 16, 17, 18, 19 or 20). In another aspect, n is from 10 to 18 (or 10, 11, 12, 13, 14, 15, 16, 17 or 18). In a related aspect, n is about 16. In yet another related aspect, the first aptamer is at least about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

In another aspect, the first aptamer is from about 18 to about 100 nucleotides in length (or 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the first aptamer comprises a nucleic acid molecule having a sequence selected from the group consisting of SEQ ID NOs: 1-8 and 10-12, wherein W is a C-5 modified pyrimidine.

In another aspect, the second aptamer comprises a nucleic acid molecule having the sequence of GGCWWCGGG-WACCWAWWAWNGGWWWAGCC(N)$_n$GWC (SEQ ID NO: 14), wherein W is independently, for each occurrence, a C-5 modified pyrimidine, N is any unmodified or modified nucleotide, and n is 0, 1, 2, 3, 4, or 5. In a related aspect, n is 2. In a related aspect, the second aptamer is at least about 32, 33, 34, 35, 36, 37, 38, 39, 40, 41, 42, 43, 44, 45, 46, 47, 48, 49 or 50 nucleotides in length. In yet another related aspect, the second aptamer is at from about 32 to about 100 nucleotides in length (or 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the second aptamer comprises a nucleic acid molecule having the sequence of AWCWGGWWC(N)$_n$AWCWGGWWWWWAAG (SEQ ID NO:15), wherein W is independently, for each occurrence, a C-5 modified pyrimidine, N is any unmodified or modified nucleotide, and n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In a related aspect, n is from 5 to 20 (or 5, 6, 7, 8, 9, 10, 11, 12, 13, 14, 15, 16, 17, 18, 19 or 20). In another aspect, n is from 10 to 18 (or 10, 11, 12, 13, 14, 15, 16, 17 or 18). In a related aspect, n is about 16.

In another aspect, the second aptamer is at least about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

In another aspect, the second aptamer is from about 18 to about 100 nucleotides in length (or 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the second aptamer comprises a nucleic acid molecule having a sequence selected from the group consisting of SEQ ID NOs: 1-8 and 10-12, wherein W is a C-5 modified pyrimidine.

In another aspect, the C-5 modified pyrimidine is selected from the group consisting of 5-(N-benzylcarboxyamide)-2'-deoxycytidine (BndC); 5-(N-2-phenylethylcarboxyamide)-2'-deoxycytidine (PEdC); 5-(N-3-phenylpropylcarboxyamide)-2'-deoxycytidine (PPdC); 5-(N-1-naphthylmethylcarboxyamide)-2'-deoxycytidine (NapdC); 5-(N-2-naphthylmethylcarboxyamide)-2'-deoxycytidine (2NapdC); 5-(N-1-naphthyl-2-ethylcarboxyamide)-2'-deoxycytidine (NEdC); 5-(N-2-naphthyl-2-ethylcarboxyamide)-2'-deoxycytidine (2NEdC); 5-(N-benzylcarboxyamide)-2'-deoxyuridine (BndU); 5-(N-isobutylcarboxyamide)-2'-deoxyuridine (iBudU); 5-(N-tryptaminocarboxyamide)-2'-deoxyuridine (TrpdU); 5-(N-[1-(3-trimethylamonium) propyl]carboxyamide)-2'-deoxyuridine chloride and 5-(N-naphthylmethylcarboxyamide)-2'-deoxyuridine (NapdU).

In another aspect, the sample is selected from the group including, but not limited to a water sample, a soil sample, a food sample, a cell sample, a culture sample, a tissue sample, a cell debris sample a biological sample and the like.

In another aspect, and for any of the embodiments disclosed herein, the concentration of the first aptamer is from about 0.5 nmol l$^{-1}$ to about 60 nmol l$^{-1}$ (or 0.5, 1, 1.5, 2, 2.5, 3, 3.2, 3.5, 4, 4.5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 36, 37, 38, 39, 40, 41, 42, 43, 44, 45, 46, 47, 48, 49, 50, 51, 52, 53, 54, 55, 56, 57, 58, 59 or 60 nmol l$^{-1}$). In a related aspect, the concentration of the first aptamer is from about 1 nmol l$^{-1}$ to about 40 nmol l$^{-1}$ (or 1, 1.5, 2, 2.5, 3, 3.2, 3.5, 4, 4.5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 36, 37, 38, 39 or 40 nmol l$^{-1}$). In a related aspect, the concentration of the first aptamer is from about 2 nmol l$^{-1}$ to about 35 nmol l$^{-1}$ (or, 2, 2.5, 3, 3.2, 3.5, 4, 4.5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5 or 35 nmol l$^{-1}$).

In a related aspect, the concentration of the first aptamer is at least 0.5 nmol$^{-1}$, 1 nmol l$^{-1}$, 2 nmol l$^{-1}$, 3 nmol l$^{-1}$, 3.2 nmol l$^{-1}$, 4 nmol l$^{-1}$, 5 nmol l$^{-1}$, 6 nmol l$^{-1}$, 7 nmol l$^{-1}$, 8 nmol l$^{-1}$, 9 nmol l$^{-1}$, 10 nmol l$^{-1}$, 11 nmol l$^{-1}$, 12 nmol l$^{-1}$, 13 nmol l$^{-1}$, 14 nmol l$^{-1}$, 15 nmol l$^{-1}$, 16 nmol l$^{-1}$, 17 nmol l$^{-1}$, 18 nmol l$^{-1}$, 19 nmol l$^{-1}$, 20 nmol l$^{-1}$, 21 nmol l$^{-1}$, 22 nmol l$^{-1}$, 23 nmol l$^{-1}$, 24 nmol l$^{-1}$, 25 nmol l$^{-1}$, 26 nmol l$^{-1}$, 27 nmol l$^{-1}$, 28 nmol l$^{-1}$, 29 nmol l$^{-1}$, 30 nmol l$^{-1}$, 31 nmol l$^{-1}$, 32 nmol l$^{-1}$, 33 nmol l$^{-1}$, 34 nmol l$^{-1}$, 35 nmol l$^{-1}$, 36 nmol l$^{-1}$, 37 nmol l$^{-1}$ 38 nmol l$^{-1}$, 39 nmol l$^{-1}$, or 40 nmol l$^{-1}$. In a related aspect, the concentration of the first aptamer is at least 1 nmol l$^{-1}$. In a related aspect, the concentration of the first aptamer is at least 3 nmol l$^{-1}$. In a related aspect, the concentration of the first aptamer is at least 5 nmol l$^{-1}$. In a related aspect, the concentration of the first aptamer is at least 10 nmol l$^{-1}$. In a related aspect, the concentration of the first aptamer is at least 20 nmol l$^{-1}$. In a related aspect, the concentration of the first aptamer is at least 30 nmol l$^{-1}$. In a related aspect, the concentration of the first aptamer is at least 32 nmol l$^{-1}$.

In another aspect, and for any of the embodiments disclosed herein, the concentration of the second aptamer is from about 5 nM to about 200 nm (or 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195 or 200 nM). In a related aspect, the concentration of the second aptamer is from about 2.5 nM to about 100 nM (or 2.5, 5, 10, 15, 20, 25, 30, 35, 40, 45, 50, 55, 60, 65, 70, 75, 80, 85, 90, 95 or 100 nM). In a related aspect, the concentration of the second aptamer is from about 10 nM to about 100 nM (or 10, 15, 20, 25, 30, 35, 40, 45, 50, 55, 60, 65, 70, 75, 80, 85, 90, 95 or 100 nM).

In a related aspect, the concentration of the second aptamer is at least 2.5 nM, 3 nM, 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM or 100 nM. In a related aspect, the concentration of the second aptamer is at least 2 nM. In a related aspect, the concentration of the second aptamer is at least 2.5 nM. In a related aspect, the concentration of the second aptamer is at least 5 nM. In a related aspect, the concentration of the second aptamer is at least 10 nM. In a related aspect, the concentration of the second aptamer is at least 20 nM. In a related aspect, the concentration of the second aptamer is at least 30 nM. In a related aspect, the concentration of the second aptamer is at least 40 nM. In a related aspect, the concentration of the second aptamer is at least 50 nM. In a related aspect, the concentration of the second aptamer is at least 60 nM. In a related aspect, the concentration of the second aptamer is at least 70 nM. In a related aspect, the concentration of the second aptamer is at least 80 nM. In a related aspect, the concentration of the second aptamer is at least 90 nM. In a related aspect, the concentration of the second aptamer is at least 100 nM.

The present disclosure further describes a nucleic acid molecule comprising at least about 15 to at least about 100 nucleotides (or at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides), at least one C-5 modified pyrimidine, and is capable of binding to a cell-surface protein of a microorganism.

In another aspect, the nucleic acid molecule comprises from about 15 to about 50 nucleotides (or 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides).

In another aspect, the nucleic acid molecule comprises at least 2, 3, 4, 5, 6, 7, 8, 9, 10, 11, 12, 13, 14, 15, 16, 17, 18, 19, 20, or 21 C-5 modified pyrimidines.

In another aspect, the nucleic acid molecule comprises at least 10%, 15%, 20%, 25%, 30%, 35%, 40%, 45%, 50% or more C-5 modified pyrimidines.

In another aspect, the nucleic acid molecule is capable of binding to the cell-surface protein with an equilibrium binding constant ($K_d$) of from about 0.03 nM to about 4.7 nM (or 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7 nM)

In another aspect, nucleic acid molecule is capable of binding to the cell-surface protein with an equilibrium binding constant (Kd) of at least about 0.03, 0.07, 0.08, 0.14, 0.15, 0.16, 0.22, 0.35, 0.47, 0.63, 0.73, 0.79, 0.84, 1.3, 1.35, 1.98, 2.17, 3.9 and 4.73 nM.

In another aspect, the C-5 modified pyrimidine is selected from the group consisting of 5-(N-benzylcarboxamide)-2'-deoxycytidine (BndC); 5-(N-2-phenylethylcarboxyamide)-2'-deoxycytidine (PEdC); 5-(N-3-phenylpropylcarboxyamide)-2'-deoxycytidine (PPdC); 5-(N-1-naphthylmethylcarboxyamide)-2'-deoxycytidine (NapdC); 5-(N-2-naphthylmethylcarboxyamide)-2'-deoxycytidine (2NapdC); 5-(N-1-naphthyl-2-ethylcarboxyamide)-2'-deoxycytidine (NEdC); 5-(N-2-naphthyl-2-ethylcarboxyamide)-2'-deoxycytidine (2NEdC); 5-(N-benzylcarboxyamide)-2'-deoxyuridine (BndU); 5-(N-isobutylcarboxyamide)-2'-deoxyuridine (iBudU); 5-(N-tryptaminocarboxyamide)-2'-deoxyuridine (TrpdU); 5-(N-[1-(3-trimethylamonium) propyl]carboxyamide)-2'-deoxyuridine chloride and 5-(N-naphthylmethylcarboxyamide)-2'-deoxyuridine (NapdU).

In another aspect, the microorganism is selected from the group consisting of a bacterial cell, parasite and virus.

In another aspect, the microorganism is a bacterial cell. In a related aspect, the bacterial cell is pathogenic.

In another aspect, the bacterial cell is a *Staphylococcus* cell. In a related aspect, the bacterial cell is a *Staphylococcus aureus* cell.

In another aspect, the cell-surface protein is a bacterial cell-surface protein.

In another aspect, the cell-surface protein is selected from the group consisting of SPA, ClfA, ClfB, FnbA, FnbB, IsdA, IsdB, IsdC, IsdH and SasD.

In another aspect, the first cell-surface protein is selected from the group consisting of SPA and ClfA.

In another aspect, the nucleic acid molecule comprises the sequence of GGCWWCGGGWACCWAWWAWNGGWW-WAGCC(N)$_n$GWC (SEQ ID NO: 14), wherein W is independently, for each occurrence, a C-5 modified pyrimidine, N is any unmodified or modified nucleotide, and n is 0, 1, 2, 3, 4 or 5. In a related aspect, n is 2.

In another aspect, the nucleic acid molecule is at least about 32, 33, 34, 35, 36, 37, 38, 39, 40, 41, 42, 43, 44, 45, 46, 47, 48, 49 or 50 nucleotides in length.

In another aspect, the nucleic acid molecule is at from about 32 to about 100 nucleotides in length (or 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the nucleic acid molecule comprises the sequence of AWCWGGWWC(N)$_n$AWCWGGWWWW-WAAG (SEQ ID NO:15), wherein W is independently, for each occurrence, a C-5 modified pyrimidine, N is any unmodified or modified nucleotide, and n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In a related aspect, n is from 5 to 20 (or 5, 6, 7, 8, 9, 10, 11, 12, 13, 14, 15, 16, 17, 18, 19 or 20). In another aspect, n is from 10 to 18 (or 10, 11, 12, 13, 14, 15, 16, 17 or 18). In a related aspect, n is about 16.

In another aspect, the nucleic acid molecule is at least about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

In another aspect, the nucleic acid molecule is from about 18 to about 100 nucleotides in length (or 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the nucleic acid molecule comprises a nucleic acid molecule having a sequence selected from the group consisting of SEQ ID NOs: 1-8 and 10-12, wherein W is a C-5 modified pyrimidine.

In another aspect, the C-5 modified pyrimidine is selected from the group consisting of 5-(N-benzylcarboxyamide)-2'-deoxycytidine (BndC); 5-(N-2-phenylethylcarboxyamide)-2'-deoxycytidine (PEdC); 5-(N-3-phenylpropylcarboxyamide)-2'-deoxycytidine (PPdC); 5-(N-1-naphthylmethylcarboxyamide)-2'-deoxycytidine (NapdC); 5-(N-2-naphthylmethylcarboxyamide)-2'-deoxycytidine (2NapdC); 5-(N-1-naphthyl-2-ethylcarboxyamide)-2'-deoxycytidine (NEdC); 5-(N-2-naphthyl-2-ethylcarboxyamide)-2'-deoxycytidine (2NEdC); 5-(N-benzylcarboxyamide)-2'-deoxyuridine (BndU); 5-(N-isobutylcarboxyamide)-2'-deoxyuridine (iBudU); 5-(N-tryptaminocarboxyamide)-2'-deoxyuridine (TrpdU); 5-(N-[1-(3-trimethylamonium) propyl]carboxyamide)-2'-deoxyuridine chloride and 5-(N-naphthylmethylcarboxyamide)-2'-deoxyuridine (NapdU).

The present disclosure further describes a kit for detecting the presence or absence of a microorganism in a sample comprising a nucleic acid molecule as described above.

The foregoing and other objects, features, and advantages of the invention will become more apparent from the following detailed description, which proceeds with reference to the accompanying figures.

BRIEF DESCRIPTION OF THE DRAWINGS

In FIG. 1A the aptamer concentration was fixed at 20 nmol l$^{-1}$ to capture cells in a 0.1 ml sample. (■) 5000 CFU, (▩) 500 CFU, and (▨) 50 CFU. In FIG. 1B the cell density was fixed at 6600 CFU in a 0.1 ml sample and the capture aptamer concentrations were varied. (■) 32 nmol l$^{-1}$, (▩) 10 nmol l$^{-1}$, (▨) 3.2 nmol l$^{-1}$, (□) 1 nmol l$^{-1}$, and (□) 0.32 nmol$^{-1}$. The efficiency of capture was calculated via quantitative culture.

DETAILED DESCRIPTION

I. Terms and Methods

Figure 1A:
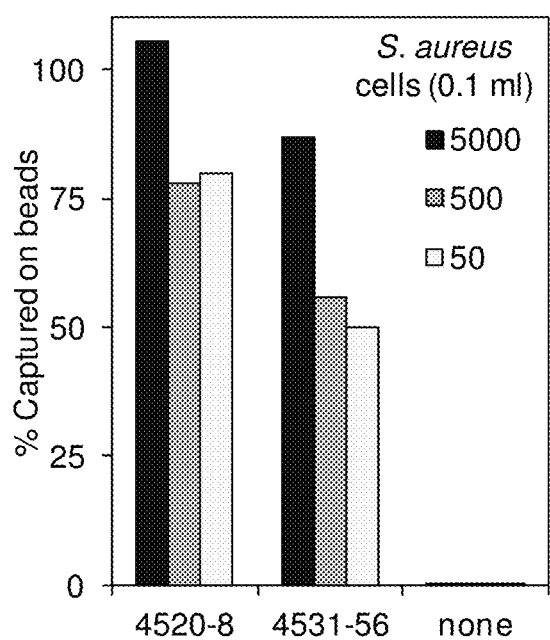
FIGS. 1A-B show the capture of *Staphylococcus aureus* bacteria with SpA aptamers immobilized on paramagnetic beads. The efficiency of cell capture was calculated via quantitative culture of the beads.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Aptamer: The term aptamer, as used herein, refers to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule.

Aptamer-Affinity Complex: As used herein, the terms "aptamer-target affinity complex", "aptamer affinity complex" or "aptamer complex" or "complex" refer to a non-covalent complex that is formed by the interaction of an aptamer with its target molecule. "Aptamer-target affinity complexes", "aptamer affinity complexes" or "aptamer complexes" or "complexes" refer to more than one such set of complexes. An aptamer-target affinity complex, aptamer affinity complex or aptamer complex or complex can generally be reversed or dissociated by a change in an environmental condition, e.g., an increase in temperature, an increase in salt concentration, or an addition of a denaturant. If desired; however, such complexes may be a covalent interaction.

Amplifiable: The term amplifiable, as used herein, refers to a molecule (e.g., nucleic acid molecule or aptamer) that is capable of being duplicated or copied to make more copies of the molecule.

Analog: The term analog, as used herein, refers to a structural chemical analog as well as a functional chemical analog. A structural chemical analog is a compound having a similar structure to another chemical compound but differing by one or more atoms or functional groups. This difference may be a result of the addition of atoms or functional groups, absence of atoms or functional groups, the replacement of atoms or functional groups or a combination thereof. A functional chemical analog is a compound that has similar chemical, biochemical and/or pharmacological properties. The term analog may also encompass S and R stereoisomers of a compound.

Bioactivity: The term bioactivity, as used herein, refers to one or more intercellular, intracellular or extracellular process (e.g., cell-cell binding, ligand-receptor binding, cell signaling, etc.) which can impact physiological or pathophysiological processes.

Biological Sample: A biological sample, as used herein, refers to "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, lung washes, BAL (bronchoalveolar lavage), thyroid, breast, and liver. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

C-5 Modified Pyrimidine: C-5 modified pyrimidine (or C-5 modified nucleotide), as used herein, refers to a pyrimidine with a modification at the C-5 position. Examples of a C-5 modified pyrimidine include those described in U.S. Pat. Nos. 5,719,273 and 5,945,527, as well as, U.S. Provisional Application Ser. No. 61/422,957, filed Dec. 14, 2010, entitled "Nuclease Resistant Oligonucleotides." Additional examples are provided herein.

Cell-Surface Protein: Cell-surface protein, as used herein, refers to a protein that is expressed on the surface of a cell, cell membrane, cell wall envelope, or has a domain that is exposed on the outside surface of the cell, on the outside cell membrane or cell wall envelope with another part or domain of the protein expressed within the cell membrane or cell wall envelope and/or in the intracellular space of a cell.

Consensus Sequence: Consensus sequence, as used herein, refers to a nucleotide sequence that represents the most frequently observed nucleotide found at each position of a series of nucleic acid sequences subject to a sequence alignment.

Covalent Bond: Covalent bond or interaction refers to a chemical bond that involves the sharing of at least a pair of electrons between atoms.

Enrich: The term enrich (or enrichment), as used herein, means to subject a sample to a process such that the proportional representation of at least one component (e.g., the complex or aptamer-target complexes) or group of components is resultantly enhanced compared to another component or group of components. Enrich may mean to enrich one component by at least 5%, 10%, 20%, 30%, 40%, 50%, 60%, 70%, 80% compared to another component.

Inhibit: The term inhibit, as used herein, means to prevent or reduce the expression of a peptide or a polypeptide to an extent that the peptide or polypeptide no longer has measurable activity or bioactivity; or to reduce the stability and/or reduce or prevent the activity of a peptide or a polypeptide to an extent that the peptide or polypeptide no longer has measurable activity or bioactivity.

Microorganism: The term microorganism, as used herein, refers to a single cell or multicellular organism and may include bacteria, archaea, protozoa, fungi, algae, microscopic plants, rotifers, planarians viruses.

Modified: The term modified (or modify or modification) and any variations thereof, when used in reference to an oligonucleotide, means that at least one of the four constituent nucleotide bases (i.e., A, G, T/U, and C) of the oligonucleotide is an analog or ester of a naturally occurring nucleotide.

Modulate: The term modulate, as used herein, means to alter the expression level of a peptide, protein or polypeptide by increasing or decreasing its expression level relative to a reference expression level, and/or alter the stability and/or activity of a peptide, protein or polypeptide by increasing or decreasing its stability and/or activity level relative to a reference stability and/or activity level.

Non-covalent Bond: Non-covalent bond or non-covalent interaction refers to a chemical bond or interaction that does not involve the sharing of pairs of electrons between atoms. Examples of non-covalent bonds or interactions include hydrogen bonds, ionic bonds (electrostatic bonds), van der Waals forces and hydrophobic interactions.

Nucleic Acid: Nucleic acid, as used herein, refers to any nucleic acid sequence containing DNA, RNA and/or analogs thereof and may include single, double and multi-stranded forms. The terms "nucleic acid", "oligo", "oligonucleotide" and "polynucleotide" may be used interchangeably.

Pharmaceutically Acceptable: Pharmaceutically acceptable, as used herein, means approved by a regulatory agency of a federal or a state government or listed in the U.S. Pharmacopoeia or other generally recognized pharmacopoeia for use in animals and, more particularly, in humans.

Pharmaceutically Acceptable Salt: Pharmaceutically acceptable salt or salt of a compound (e.g., aptamer), as used herein, refers to a product that contains an ionic bond and is typically produced by reacting the compound with either an acid or a base, suitable for administering to an individual. A pharmaceutically acceptable salt can include, but is not limited to, acid addition salts including hydrochlorides, hydrobromides, phosphates, sulfates, hydrogen sulfates, alkylsulfonates, arylsulfonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

Pharmaceutical Composition: Pharmaceutical composition, as used herein, refers to formulation comprising an aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

SELEX: The term SELEX, as used herein, refers to generally to the selection for nucleic acids that interact with a target molecule in a desirable manner, for example binding with high affinity to a protein; and the amplification of those selected nucleic acids. SELEX may be used to identify aptamers with high affinity to a specific target molecule. The term SELEX and "SELEX process" may be used interchangeably.

Sequence Identity: Sequence identity, as used herein, in the context of two or more nucleic acid sequences is a function of the number of identical nucleotide positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST). For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)). As used herein, when describing the percent identity of a nucleic acid, such as a Spa (or SPA) aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence.

Solid Support: Solid support refers to any substrate having a surface to which molecules may be attached, directly or indirectly, through either covalent or non-covalent bonds. The solid support may include any substrate material that is capable of providing physical support for the capture elements or probes that are attached to the surface. The material is generally capable of enduring conditions related to the attachment of the capture elements or probes to the surface and any subsequent treatment, handling, or processing encountered during the performance of an assay. The materials may be naturally occurring, synthetic, or a modification of a naturally occurring material. Suitable solid support materials may include silicon, a silicon wafer chip, graphite, mirrored surfaces, laminates, membranes, ceramics, plastics (including polymers such as, e.g., poly(vinyl chloride), cyclo-olefin copolymers, agarose gels or beads, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, Langmuir Blodgett films, a flow through chip, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads, crosslinked beaded Sepharose® or agarose resins, or copolymers of crosslinked bis-acrylamide and azalactone. Other beads include nanoparticles, polymer beads, solid core beads, paramagnetic beads, or microbeads. Any other materials known in the art that are capable of having one or more functional groups, such as any of an amino, carboxyl, thiol, or hydroxyl functional group, for example, incorporated on its surface, are also contemplated.

The material used for a solid support may take any of a variety of configurations ranging from simple to complex. The solid support can have any one of a number of shapes, including a strip, plate, disk, rod, particle, bead, tube, well (microtiter), and the like. The solid support may be porous or non-porous, magnetic, paramagnetic, or non-magnetic, polydisperse or monodisperse, hydrophilic or hydrophobic. The solid support may also be in the form of a gel or slurry of closely-packed (as in a column matrix) or loosely-packed particles.

In one embodiment, the solid support with attached capture element is used to capture tagged aptamer-target affinity complexes or aptamer-target covalent complexes from a test mixture. In one particular example, when the tag is a biotin moiety, the solid support could be a streptavidin-coated bead or resin such as Dynabeads M-280 Streptavidin, Dynabeads MyOne Streptavidin, Dynabeads M-270 Streptavidin (Invitrogen), Streptavidin Agarose Resin (Pierce), Streptavidin Ultralink Resin, MagnaBind Streptavidin Beads (Thermo-Fisher Scientific), BioMag Streptavidin, ProMag Streptavidin, Silica Streptavidin (Bangs Laboratories), Streptavidin Sepharose High Performance (GE Healthcare), Streptavidin Polystyrene Microspheres (Microspheres-Nanospheres), Streptavidin Coated Polystyrene Particles (Spherotech), or any other streptavidin coated bead or resin commonly used by one skilled in the art to capture biotin-tagged molecules.

One object of the instant invention is to convert a protein signal into an aptamer signal. As a result the quantity of aptamers collected/detected is indicative of, and may be directly proportional to, the quantity of target molecules bound and to the quantity of target molecules in the sample. A number of detection schemes can be employed without eluting the aptamer-target affinity or aptamer-target covalent complex from the second solid support after the second partitioning or catch. In addition to the following embodiments of detection methods, other detection methods will be known to one skilled in the art.

Many detection methods require an explicit label to be incorporated into the aptamer prior to detection. In these embodiments, labels, such as, for example, fluorescent or chemiluminescent dyes can be incorporated into aptamers either during or post synthesis using standard techniques for nucleic acid synthesis. Radioactive labels can be incorporated either during synthesis or post synthesis using standard enzyme reactions with the appropriate reagents. Labeling can also occur after the second partitioning and elution by using suitable enzymatic techniques. For example, using a primer with the above mentioned labels, PCR will incorporate labels into the amplification product of the eluted aptamers. When using a gel technique for quantification, different size mass labels can be incorporated using PCR as well. These mass labels can also incorporate different fluorescent or chemiluminescent dyes for additional multiplexing capacity. Labels may be added indirectly to aptamers by using a specific tag incorporated into the aptamer, either during synthesis or post synthetically, and then adding a probe that associates with the tag and carries the label. The labels include those described above as well as enzymes used in standard assays for colorimetric readouts, for example. These enzymes work in combination with enzyme substrates and include enzymes such as, for example, horseradish peroxidase (HRP) and alkaline phosphatase (AP). Labels may also include materials or compounds that are electrochemical functional groups for electrochemical detection.

For example, the aptamer may be labeled, as described above, with a radioactive isotope such as $^{32}$P prior to contacting the test sample. Employing any one of the four basic assays, and variations thereof as discussed above, aptamer detection may be simply accomplished by quantifying the radioactivity on the second solid support at the end of the assay. The counts of radioactivity will be directly proportional to the amount of target in the original test sample. Similarly, labeling an aptamer with a fluorescent dye, as described above, before contacting the test sample allows for a simple fluorescent readout directly on the second solid support. A chemiluminescent label or a quantum dot can be similarly employed for direct readout from the second solid support, requiring no aptamer elution.

In another embodiment, the amount or concentration of the aptamer-target affinity complex (or aptamer-target covalent complex) is determined using a "molecular beacon" during a replicative process (see, e.g., Tyagi et al., Nat. Biotech. J. 6:49 53, 1998; U.S. Pat. No. 5,925,517). A molecular beacon is a specific nucleic acid probe that folds into a hairpin loop and contains a fluorophore on one end and a quencher on the other end of the hairpin structure such that little or no signal is generated by the fluorophore when the hairpin is formed. The loop sequence is specific for a target polynucleotide sequence and, upon hybridizing to the aptamer sequence the hairpin unfolds and thereby generates a fluorescent signal.

For multiplexed detection of a small number of aptamers still bound to the second solid support, fluorescent dyes with different excitation/emission spectra can be employed to detect and quantify two, or three, or five, or up to ten individual aptamers. Similarly different sized quantum dots can be employed for multiplexed readouts. The quantum dots can be introduced after partitioning free aptamer from the second solid support. By using aptamer specific hybridization sequences attached to unique quantum dots multiplexed readings for 2, 3, 4, 5, and up to 10 aptamers can be performed. Labeling different aptamers with different radioactive isotopes that can be individually detected, such as $^{32}$P, $^{3}$H, $^{13}$C, and $^{35}$S, can also be used for limited multiplex readouts.

In one embodiment, a standard DNA hybridization array, or chip, is used to hybridize each aptamer or photoaptamer to a unique or series of unique probes immobilized on a slide or chip such as Agilent arrays, Illumina BeadChip Arrays, NimbleGen arrays or custom printed arrays. Each unique probe is complementary to a sequence on the aptamer. The complementary sequence may be a unique hybridization tag incorporated in the aptamer, or a portion of the aptamer sequence, or the entire aptamer sequence. The aptamers released from the solid support after the second partitioning or catch are added to an appropriate hybridization buffer and processed using standard hybridization methods. For example, the aptamer solution is incubated for 12 hours with a DNA hybridization array at about 60° C. to ensure stringency of hybridization. The arrays are washed and then scanned in a fluorescent slide scanner, producing an image of the aptamer hybridization intensity on each feature of the array. Image segmentation and quantification is accomplished using image processing software, such as ArrayVision. In one embodiment, multiplexed aptamer assays can be detected using up to 25 aptamers, up to 50 aptamers, up to 100 aptamers, up to 200 aptamers, up to 500 aptamers, up to 1000 aptamers, and up to 10,000 aptamers.

In one embodiment, addressable micro-beads having unique DNA probes complementary to the aptamers as described above are used for hybridization. The micro-beads may be addressable with unique fluorescent dyes, such as Luminex beads technology, or use bar code labels as in the Illumina VeraCode technology, or laser powered transponders. In one embodiment, the aptamers released from the second solid support are added to an appropriate hybridization buffer and processed using standard micro-bead hybridization methods. For example, the aptamer solution is incubated for two hours with a set of micro-beads at about 60° C. to ensure stringency of hybridization. The solutions are then processed on a Luminex instrument which counts the individual bead types and quantifies the aptamer fluorescent signal. In another embodiment, the VeraCode beads are contacted with the aptamer solution and hybridized for two hours at about 60° C. and then deposited on a gridded surface and scanned using a slide scanner for identification and fluorescence quantification. In another embodiment, the transponder micro-beads are incubated with the aptamer sample at about 60° C. and then quantified using an appropriate device for the transponder micro-beads. In one embodiment, multiplex aptamer assays can be detected by hybridization to micro-beads using up to 25 aptamers, up to 50 aptamers, up to 100 aptamers, up to 200 aptamers, and up to 500 aptamers.

The sample containing the eluted aptamers can be processed to incorporate unique mass tags along with fluorescent labels as described above. The mass labeled aptamers are then injected into a CGE instrument, essentially a DNA sequencer, and the aptamers are identified by their unique masses and quantified using fluorescence from the dye incorporated during the labeling reaction. One exemplary example of this technique has been developed by Althea Technologies.

In many of the methods described above, the solution of aptamers can be amplified and optionally tagged before quantification. Standard PCR amplification can be used with the solution of aptamers eluted from the second solid support. Such amplification can be used prior to DNA array hybridization, micro-bead hybridization, and CGE readout.

In another embodiment, the aptamer-target affinity complex (or aptamer-target covalent complex) is detected and/or quantified using Q-PCR. As used herein, "Q-PCR" refers to a PCR reaction performed in such a way and under such controlled conditions that the results of the assay are quantitative, that is, the assay is capable of quantifying the amount or concentration of aptamer present in the test sample.

In one embodiment, the amount or concentration of the aptamer-target affinity complex (or aptamer-target covalent complex) in the test sample is determined using TaqMan® PCR. This technique generally relies on the 5'-3' exonuclease activity of the oligonucleotide replicating enzyme to generate a signal from a targeted sequence. A TaqMan probe is selected based upon the sequence of the aptamer to be quantified and generally includes a 5'-end fluorophore, such as 6-carboxyfluorescein, for example, and a 3'-end quencher, such as, for example, a 6-carboxytetramethylfluorescein, to generate signal as the aptamer sequence is amplified using polymerase chain reaction (PCR). As the polymerase copies the aptamer sequence, the exonuclease activity frees the fluorophore from the probe, which is annealed downstream from the PCR primers, thereby generating signal. The signal increases as replicative product is produced. The amount of PCR product depends upon both the number of replicative cycles performed as well as the starting concentration of the aptamer.

In another embodiment, the amount or concentration of an aptamer-target affinity complex (or aptamer-target covalent complex) is determined using an intercalating fluorescent dye during the replicative process. The intercalating dye, such as, for example, SYBR® green, generates a large fluorescent signal in the presence of double-stranded DNA as compared to the fluorescent signal generated in the presence of single-stranded DNA. As the double-stranded DNA product is formed during PCR, the signal produced by the dye increases. The magnitude of the signal produced is dependent upon both the number of PCR cycles and the starting concentration of the aptamer.

In another embodiment, the aptamer-target affinity complex (or aptamer-target covalent complex) is detected and/or quantified using mass spectrometry. Unique mass tags can be introduced using enzymatic techniques described above. For mass spectroscopy readout, no detection label is required, rather the mass itself is used to both identify and, using techniques commonly used by those skilled in the art, quantified based on the location and area under the mass peaks generated during the mass spectroscopy analysis. An example using mass spectroscopy is the MassARRAY® system developed by Sequenom.

SOMAmer: The term SOMAmer (or SOMAmer reagent), as used herein, refers to an aptamer having improved off-rate characteristics. SOMAmer reagents are alternatively referred to as Slow Off-Rate Modified Aptamers, and may be selected via the improved SELEX methods described in U.S. Publication No. 20090004667, entitled "Method for Generating Aptamers with Improved Off-Rates", which is incorporated by reference in its entirety. Slow Off-Rate Modified Aptamer refers to an aptamer (including an aptamers comprising at least one nucleotide with a hydrophobic modification) with an off-rate ($t_{1/2}$) of ≥30 minutes, ≥60 minutes, ≥90 minutes, ≥120 minutes, ≥150 minutes, ≥180 minutes, ≥210 minutes, or ≥240 minutes.

Spacer Sequence: Spacer sequence, as used herein, refers to any sequence comprised of small molecule(s) covalently bound to the 5'-end, 3'-end or both 5' and 3' ends of the nucleic acid sequence of an aptamer. Exemplary spacer sequences include, but are not limited to, polyethylene glycols, hydrocarbon chains, and other polymers or copolymers that provide a molecular covalent scaffold connecting the consensus regions while preserving target-aptamer binding activity. In certain aspects, the spacer sequence may be covalently attached to the aptamer through standard linkages such as the terminal 3' or 5' hydroxyl, 2' carbon, or base modification such as the C5-position of pyrimidines, or C8 position of purines.

Substantially Remove: Substantially remove, as used herein, means to remove at least 5%, 10%, 15%, 20%, 25%, 30%, 35%, 40%, 45%, 50%, 55%, 60%, 65%, 70%, 75%, 80% or more of a component or components (e.g., material not bound to the solid support) compared to another component (e.g., material bound to the solid support or aptamer-target complex).

Tag: As disclosed herein, an aptamer can further comprise a "tag," which refers to a component that provides a means for attaching or immobilizing an aptamer (and any target molecule that is bound to it) to a solid support and/or a means for detecting the aptamer or the complex (aptamer-target complex). A "tag" is a moiety that is capable of associating with a "capture element". "Tags" or "capture elements" refers to more than one such set of components. The tag can be attached to or included in the aptamer by any suitable method. Generally, the tag allows the aptamer to associate, either directly or indirectly, with a capture element or receptor that is attached to the solid support. The capture element is typically chosen (or designed) to be highly specific in its interaction with the tag and to retain that association during subsequent processing steps or procedures. A tag can enable the localization of an aptamer-target affinity complex (or covalent aptamer-target affinity complex) to a spatially defined address on a solid support. Different tags, therefore, can enable the localization of different aptamer-target covalent complexes to different spatially defined addresses on a solid support. A tag can be a polynucleotide, a polypeptide, a peptide nucleic acid, a locked nucleic acid, an oligosaccharide, a polysaccharide, an antibody, an affibody, an antibody mimic, a cell receptor, a ligand, a lipid, biotin, polyhistidine, or any fragment or derivative of these structures, any combination of the foregoing, or any other structure with which a capture element (or linker molecule, as described below) can be designed or configured to bind or otherwise associate with specificity. In the context of a tag for detection purposes, the tag may be a dye, a quantum dot, a radiolabel, PCR primer sites, an electrochemical functional group, and an enzyme plus a detectable enzyme substrate. A tag may comprise two distinct domains or regions that attach to the aptamer to allow the aptamer to be detected (e.g. PCR primer sites would include two distinct nucleic acid sequence that may attach to the 5' or 3' end of the aptamer or in some cases where the one PCR primer site attaches to the 5' end of the aptamer and the a second PCR primer set (of the pair) attach to the 3' end of the aptamer.

Generally, the tag may be added to the aptamer either pre- or post-SELEX. In one embodiment, the tag is included on the 5'-end of the aptamer. In another embodiment, the tag is included on the 3'-end of the aptamer. In yet another embodiment, tags may be included on both the 3' and 5' ends of the aptamers. In another embodiment, the tag may be an internal segment of the aptamer.

Target Molecule: Target molecule (or target), as used herein, refers to any compound or molecule upon which a nucleic acid can act in a desirable manner (e.g., binding of the target, catalytically changing the target, reacting with the target in a way that modifies or alters the target or the functional activity of the target, covalently attaching to the target (as in a suicide inhibitor), and facilitating the reaction between the target and another molecule). Non-limiting examples of a target molecule include a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc. Virtually any chemical or biological effector may be a suitable target. Molecules of any size can serve as targets. A target can also be modified in certain ways to enhance the likelihood or strength of an interaction between the target and the nucleic acid. A target may also include any minor variation of a particular compound or molecule, such as, in the case of a protein, for example, variations in its amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. In some embodiments, the modified nucleotides lead to predominantly hydrophobic interactions of aptamers with protein targets resulting in high binding efficiency and stable co-crystal complexes. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in some embodiments ranging from about 10 to about 80 kDa, PEG polymers in some embodiments ranging from about 20 to about 60 kDa, or other hydrophilic or hydrophobic biological or synthetic polymers. In some embodiments, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

As used herein, the term "nuclease" refers to an enzyme capable of cleaving the phosphodiester bond between nucleotide subunits of an oligonucleotide. As used herein, the term "endonuclease" refers to an enzyme that cleaves phosphodiester bond(s) at a site internal to the oligonucleotide. As used herein, the term "exonuclease" refers to an enzyme which cleaves phosphodiester bond(s) linking the end nucleotides of an oligonucleotide. Biological fluids typically contain a mixture of both endonucleases and exonucleases.

As used herein, the terms "nuclease resistant" and "nuclease resistance" refers to the reduced ability of an oligonucleotide to serve as a substrate for an endo- or exonuclease, such that, when contacted with such an enzyme, the oligonucleotide is either not degraded or is degraded more slowly than an oligonucleotide composed of unmodified nucleotides.

As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

As used herein, A, C, G, U and T denote dA, dC, dG, dU and dT respectively, unless otherwise specified.

As used herein, "nucleic acid ligand," "aptamer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In some embodiments, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions.

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

A "SPA aptamer" is an aptamer that is capable of binding to the SPA protein. The term "SpA", "SPA" or "Spa" may be used interchangeably to refer to the SPA protein or SPA aptamer.

A "ClfA aptamer" is an aptamer that is capable of binding to the ClfA protein.

A "ClfB aptamer" is an aptamer that is capable of binding to the ClfB protein.

A "FnbA aptamer" is an aptamer that is capable of binding to the FnbA protein.

A "FnbB aptamer" is an aptamer that is capable of binding to the FnbB protein.

A "IsdA aptamer" is an aptamer that is capable of binding to the IsdA protein.

A "IsdB aptamer" is an aptamer that is capable of binding to the IsdB protein.

A "IsdC aptamer" is an aptamer that is capable of binding to the IsdC protein.

A "IsdH aptamer" is an aptamer that is capable of binding to the IsdH protein.

A "SasD aptamer" is an aptamer that is capable of binding to the SasD protein.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A or B, or A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated.

Also, any number range recited herein relating to any physical feature, such as polymer subunits, size or thickness, are to be understood to include any integer within the recited range, unless otherwise indicated. As used herein, "about" or "consisting essentially of mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g., "or") should be understood to mean either one, both, or any combination thereof of the alternatives Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Overview

Binding agents to specific components on the surface of microorganisms can be valuable diagnostic tools useful for different detection platforms.

Selex

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH$_2$), 2'-fluoro (2'-F), and/or 2'-O-methyl (2'-OMe). See also, U.S. Patent Application Publication 20090098549, entitled "SELEX and PHOTOSELEX", which describes nucleic acid libraries having expanded physical and chemical properties and their use in SELEX and photoSELEX.

SELEX can also be used to identify aptamers that have desirable off-rate characteristics. See U.S. Patent Application Publication 20090004667, entitled "Method for Generating Aptamers with Improved Off-Rates," which describes improved SELEX methods for generating aptamers that can bind to target molecules. As mentioned above, these slow off-rate aptamers are known as "SOMAmers." Methods for producing aptamers or SOMAmer reagents and photoaptamers or SOMAmer reagents having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers or SOMAmer reagents with improved off-rate performance.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip." These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands." After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers.

In both of these assay formats, the aptamers or SOMAmer reagents are immobilized on the solid support prior to being contacted with the sample. Under certain circumstances, however, immobilization of the aptamers or SOMAmer reagents prior to contact with the sample may not provide an optimal assay. For example, pre-immobilization of the aptamers or SOMAmer reagents may result in inefficient mixing of the aptamers or SOMAmer reagents with the target molecules on the surface of the solid support, perhaps leading to lengthy reaction times and, therefore, extended incubation periods to permit efficient binding of the aptamers or SOMAmer reagents to their target molecules. Further, when photoaptamers or photoaptamers are employed in the assay and depending upon the material utilized as a solid support, the solid support may tend to scatter or absorb the light used to effect the formation of covalent bonds between the photoaptamers or photoaptamers and their target molecules. Moreover, depending upon the method employed, detection of target molecules bound to their aptamers or photoaptamers can be subject to imprecision, since the surface of the solid support may also be exposed to and affected by any labeling agents that are used. Finally, immobilization of the aptamers or SOMAmer reagents on the solid support generally involves an aptamer or SOMAmer reagent-preparation step (i.e., the immobilization) prior to exposure of the aptamers or SOMAmer reagents to the sample, and this preparation step may affect the activity or functionality of the aptamers or SOMAmer reagents.

Aptamer assays that permit an aptamer to capture its target in solution and then employ separation steps that are designed to remove specific components of the aptamer-target mixture prior to detection have also been described (see U.S. Patent Application Publication 20090042206, entitled "Multiplexed Analyses of Test Samples"). The described aptamer assay methods enable the detection and quantification of a non-nucleic acid target (e.g., a protein target) in a test sample by detecting and quantifying a nucleic acid (i.e., a aptamer). The described methods create a nucleic acid surrogate (i.e., the aptamer) for detecting and quantifying a non-nucleic acid target, thus allowing the wide variety of nucleic acid technologies, including amplification, to be applied to a broader range of desired targets, including protein targets.

Embodiments of the SELEX process in which the target is a peptide are described in U.S. Pat. No. 6,376,190, entitled "Modified SELEX Processes Without Purified Protein."

Chemical Modifications to Aptamers

Aptamers may contain modified nucleotides that improve it properties and characteristics. Non-limiting examples of such improvements include, in vivo stability, stability against degradation, binding affinity for its target, and/or improved delivery characteristics.

Examples of such modifications include chemical substitutions at the ribose and/or phosphate and/or base positions of a nucleotide. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

Specific examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

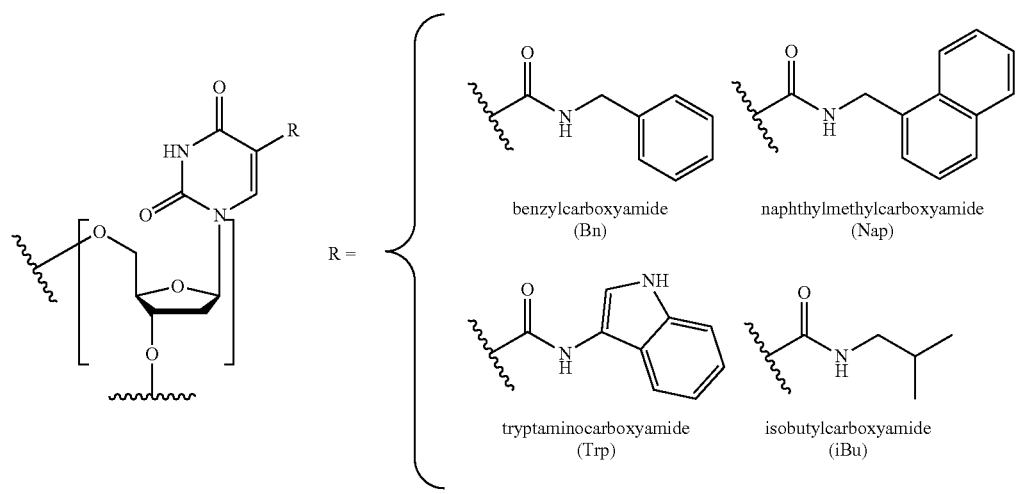

Specific examples of a C-5 modification include substitution of deoxyuridine Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxamide)-2'-deoxyuridine (BndU), 5-(N-benzylcarboxamide)-2'-O-methyluridine, 5-(N-benzylcarboxamide)-2'-fluorouridine, 5-(N-isobutylcarboxamide)-2'-deoxyuridine (iBudU), 5-(N-isobutylcarboxamide)-2'-O-methyluridine, 5-(N-isobutylcarboxamide)-2'-fluorouridine, 5-(N-tryptaminocarboxamide)-2'-deoxyuridine (TrpdU), 5-(N-tryptaminocarboxamide)-2'-O-methyluridine, 5-(N-tryptaminocarboxamide)-2'-fluorouridine, 5-(N-[1-(3-trimethylamonium) propyl] carboxyamide)-2'-deoxyuridine chloride, 5-(N-naphthylmethylcarboxamide)-2'-deoxyuridine (NapdU), 5-(N-naphthylmethylcarboxamide)-2'-O-methyluridine, 5-(N-naphthylmethylcarboxamide)-2'-fluorouridine or 5-(N-[1-(2,3-dihydroxypropyl)]carboxyamide)-2'-deoxyuridine).

If present, a modification to the nucleotide structure can be imparted before or after assembly of the polynucleotide. A sequence of nucleotides can be interrupted by non-nucleotide components. A polynucleotide can be further modified after polymerization, such as by conjugation with a labeling component.

Additional non-limiting examples of modified nucleotides (e.g., C-5 modified pyrimidine) that may be incorporated into the nucleic acid sequences of the present disclosure include the following:

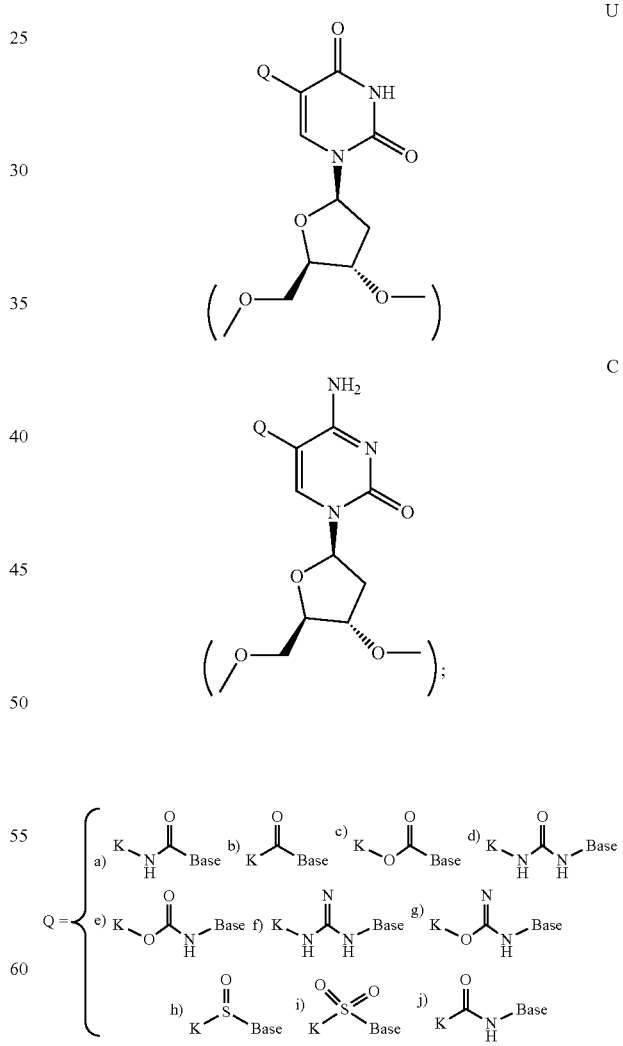

Base = Uridine (U) or Cytidine (C) (attachment is to the 5-position)
K = R' group plus $(CH_2)_n$ connecting group, where n = 0-3 wherein R' is defined as follows:

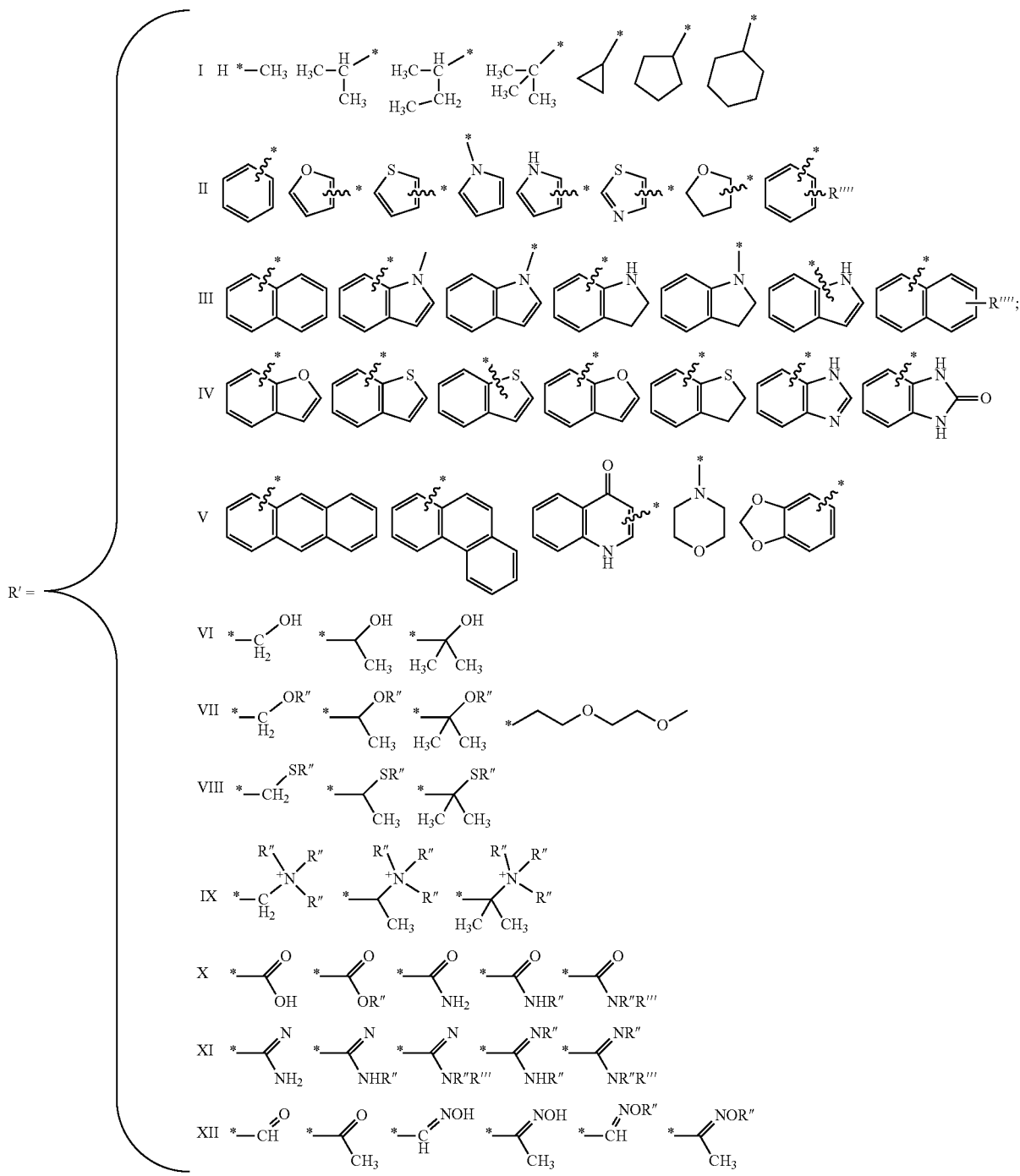

*Denotes point of attachment of the R' group to (CH2)$_n$ connecting group wherein
R"" is selected from the group consisting of a branched or linear lower alkyl (C1-C20); hydroxyl (OH), halogen (F, Cl, Br, I); nitrile (CN); boronic acid (BO$_2$H$_2$); carboxylic acid (COOH); carboxylic acid ester (COOR"); primary amide (CONH$_2$); secondary amide (CONHR"); tertiary amide (CONR"R'"); sulfonamide (SO$_2$NH$_2$); N-alkylsulfonamide (SONHR");

wherein
R", R'" are independently selected from a group consisting of a branched or linear lower alkyl (C1-C2)); phenyl (C6H5); an R'" substituted phenyl ring (R'"C6H4); wherein R"" is defined above; a carboxylic acid (COOH); a carboxylic acid ester (COOR""); wherein R"" is a branched or linear lower alkyl (C1-C20); and cycloalkyl; wherein R"=R'"=(CH2)n;
wherein n=2-10.

Further, C-5 modified pyrimidine nucleotides include the following:

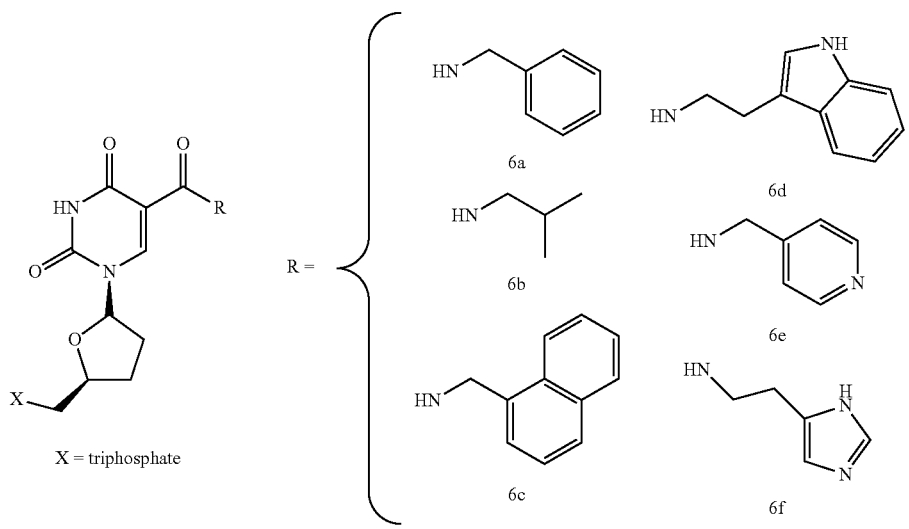

In some embodiments, the modified nucleotide confers nuclease resistance to the oligonucleotide. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

The following examples are provided to illustrate certain particular features and/or embodiments. These examples should not be construed to limit the disclosure to the particular features or embodiments described.

*Staphylococcus aureus* (Also Referred to Herein as *S. aureus*)

Staining of surface antigens for immunofluorescence microscopy has been demonstrated using antibody-fluorophore conjugates to detect relatively low numbers of *S. aureus* cells over time in in vivo infection models (Timofeyeva et al., 2014). Short peptides as specific ligands to the *S. aureus* cell surface have been identified by phage-display, and a synthetic consensus peptide (SA5-1) was able to detect approximately 100 CFU ml$^{-1}$ in a spiked biological sample using fluorescent quantum dots (Rao et al., 2013).

Major groups are the MSCRAMMs (Microbial surface components recognizing adhesive matrix molecules), the SERAMs (secretable expanded repertoire adhesive molecules), as well as other extracellular toxins and immune evasion factors (Gill et al., 2005; Speziale et al., 2009). It is possible to use whole bacterial cells for SELEX (Cao et al., 2009), or surface-associated proteins extracted from cells with LiCl, lysostaphin, or 2% SDS (Palma et al., 1998; Hussain et al., 2001; Roche et al., 2003), or released by trypsin-shaving (Ythier et al., 2012). However, the composition of the surface proteome in vitro varies between different strains and depends on media and growth phase. Furthermore, staphylococci other than *S. aureus* express closely related proteins, which may hamper the isolation of species-specific reagents without careful counter-selection.

Therefore, we chose to focus on well-conserved *S. aureus*-specific cell surface proteins that are known to be expressed in abundance and under most growth conditions, and produced these SELEX targets in recombinant form.

Proteins that are exposed on the *S. aureus* cell surface can directly interact with extracellular molecules, including drugs and antibodies, and these adhesions or immune evasion proteins represent vaccine candidate targets (Stranger-Jones et al., 2006; McCarthy and Lindsay, 2010; Dreisbach et al., 2011). The *S. aureus* cell envelope, cell wall-associated proteins and mechanisms for protein attachment, are quite well understood (Dreisbach et al., 2011). Comparison of whole genome sequences of 58 *S. aureus* strains, however, revealed variations in proteins implicated in adhesion or immune response evasion, or proteins that were missing or truncated in certain strains (McCarthy and Lindsay, 2010). Adhesins include a family of surface proteins covalently attached to the peptidoglycan via a conserved LPXTG motif (Schneewind et al., 1995). Proteomic and transcriptomic profiling of surface proteins has been shown to correlate well with adherence-phenotypes in *S. aureus* (Roche et al., 2003; Ythier et al., 2012).

The ten surface-associated proteins for which we generated aptamers include SpA, ClfA, ClfB, FnbA, FnbB, SasD, IsdA, IsdB, IsdC, and IsdH. All of these proteins are attached to the cell-wall via sortase-mediated cleavage between the threonine and the glycine of the LPXTG sortase motif and become amide-linked to the pentaglycine cross-bridge of peptidoglycan (Marraffini et al., 2006). Since our goal was to obtain binding agents to *S. aureus* cells, we produced recombinant proteins that represent the surface-exposed domains but lack the signal sequences and the repeat regions of the cell wall-embedded domain. *S. aureus* protein A (SpA) is present on the bacterial surface as well as secreted into the extracellular milieu. SpA is a potent immune evasion factor since it binds the Fc region of antibodies and the Fab regions of the B-cell receptor (IgM), thus blocking opsonophagocytosis and causing B-cell death (Falugi et al., 2013; Kobayashi and Deleo, 2013). Since SpA well-conserved in among *S. aureus* but is absent in non-pathogenic staphylococci such as *Staphylococcus epidermidis* and *Staphylococcus haemolyticus*, this protein represents an attractive diagnostic target. Clinical isolates with truncated SpA variants have been described that lack the XC region with the C-terminal sorting signal and are thus found mainly extracellular (Sorum et al., 2013). ClfA and ClfB are structurally related fibrinogen-binding proteins (McDevitt et al., 1997; Ni Eidhin et al., 1998). ClfB is one of the key factors responsible for adherence to desquamated epithelial cells of the anterior nares, and is typically produced during early exponential phase of growth (Ni Eidhin et al., 1998). FnbA and FnbB adhere to components of the extracellular matrix, both fibronectin and elastin, and are important for colonization of host tissues during infection (Roche et al., 2004). SasD is a putative adhesion protein with unknown physiological role (Roche et al., 2003; Ythier et al., 2012). Four of the proteins belong to the iron-responsive surface determinant (Isd) system that is induced in *S. aureus* under iron-limiting conditions and is important for capture of heme from hemoglobin (IsdB, IsdH) and its transport (IsdA, IsdC) across the cell wall (Mazmanian et al., 2003; Grigg et al., 2010).

As a proof-of-concept and to assess their efficiency, the aptamers generated against *S. aureus* cell surface-associated proteins were used to capture and detect *S. aureus* using qPCR and also to directly detect the cells by flow cytometry.

SOMAmer (slow off-rate modified aptamer) reagents are made from single-stranded DNA (ssDNA) that contain pyrimidine residues modified at their 5-prime position with mimics of amino acid side-chains and have quite long (>30 min) dissociation rates (Gold et al., 2010). These features lead to better affinity and better kinetic properties of aptamers compared to standard RNA or DNA aptamers. Virtually any protein can be used for SELEX (systematic evolution of ligands by exponential enrichment) to generate specific, high-affinity aptamers in multiple rounds of selection with kinetic challenge, partitioning, and amplification from a random library of modified ssDNA (Gold et al., 2010; Vaught et al., 2010). Advantages of aptamers over antibodies include exceptional thermostability in solution, lower molecular weight, higher multiplexing capabilities, chemical stability to heat, drying, and solvents, reversible renaturation, ease of reagent manufacturing, consistent lot-to-lot performance and lower cost. Aptamers have been generated to >1000 human proteins and are the basis for the SOMAscan™ proteomic platform developed by SomaLogic to measure these proteins simultaneously and with high accuracy in a small (0.1 ml) blood sample. The application of this highly multiplexed assay has led to the discovery of biomarkers in various areas of medicine (Gold et al., 2012). With respect to microbial proteins, we have previously reported on the characterization of aptamers for *Clostridium difficile* toxins and shown the wide range of potential applications of these binding agents (Ochsner et al., 2013).

Slow off-rate modified aptamer (SOMAmer reagent) reagents were generated to several *Staphylococcus aureus* cell surface-associated proteins via SELEX with multiple modified DNA libraries using purified recombinant or native proteins. High-affinity binding agents with sub-nanomolar $K_d$'s were obtained for staphylococcal protein A (SpA), clumping factors (ClfA, ClfB), fibronectin-binding proteins (FnbA, FnbB) and iron-regulated surface determinants (Isd). Further screening revealed several aptamers that specifically bound to *S. aureus* cells from all strains that were tested, but not to other staphylococci or other bacteria. SpA and ClfA aptamers proved useful for the selective capture and enrichment of *S. aureus* cells from low cell-density matrices, as shown by culture and PCR, leading to improved limits of detection and efficient removal of PCR inhibitors. Detection of *S. aureus* cells was enhanced by several orders of magnitude when the bacterial cell surface was coated with aptamers followed by qPCR of the aptamers. Furthermore, fluorescence labeled SpA aptamers demonstrated their utility as direct detection agents in flow cytometry.

Kits Comprising Aptamer Compositions

The present disclosure provides kits comprising any of the aptamers described herein. Such kits can comprise, for example, (1) at least one aptamer that binds a target; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

In another aspect this disclosure provides an aptamer sequence that binds the SPA protein represented by SEQ ID NO: 9. The nucleotide sequence may be further generalized to the following sequence:

GGCWWCGGGWACCWAWWAWNGGWWWAGCC (N)$_n$GWC (SEQ ID NO:14) wherein "W" in the sequence represents a position that may be occupied by a C-5 modified pyrimidine, and "N" represents a position that may be occupied by any unmodified or modified nucleotide, and n is from 0 to 2 (or 0, 1 or 2).

In another aspect, N is a C, T, G or A. In another aspect, N is a C, T or A.

In another aspect, the nucleotide sequence may include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides.

In another aspect this disclosure, the aptamer may be at least about 95% identical, at least about 90% identical, at least about 85% identical, at least about 80% identical, or at least about 75% identical to any of SEQ ID NO: 14. In another embodiment, the aptamer includes a sequence fragments of SEQ ID NO: 14.

In another aspect, the aptamer comprises from 1 to 50 (or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50) C-5 modified pyrimidines. In another aspect, the aptamer comprises from 5 to 30 (or 5, 6, 7, 8, 9, 10, 11, 12, 13, 14, 15, 16, 17, 18, 19, 20, 21, 22, 23, 24, 25, 26, 27, 28, 29 or 30) C-5 modified pyrimidines. In another aspect, the aptamer comprises from 10 to 15 (or from 10, 11, 12, 13, 14 or 15) C-5 modified pyrimidines.

In another aspect, the aptamer comprises from about 1% to 100% (or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) C-5 modified pyrimidines. In another aspect, the aptamer comprises from about 10% to about 50% (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50%) C-5 modified pyrimidines. In another aspect, the aptamer comprises, from about 20% to about 40% (or 20, 21, 22, 23, 24, 25, 26, 27, 28, 29, 30, 31, 32, 33, 34, 35, 36, 37, 38, 39 or 40%) C-5 modified pyrimidines. In another aspect, the aptamer comprises from about 25% to about 35% (or 25, 26, 27, 28, 29, 30, 31, 32, 33, 34, 35%) C-5 modified pyrimidines. In another aspect, the aptamer comprises from about 27% to about 33% (or 27, 28, 29, 30, 31, 32 or 33%) C-5 modified pyrimidines. In another aspect, the aptamer comprises from about 37% to about 43% (or 37, 38, 39, 40, 41, 42, 43%) C-5 modified pyrimidines.

In another aspect, W may represent a C-5 modified uridine or cytidine.

In another aspect, W may represent a C-5 modified pyrimidine illustrated immediately below:

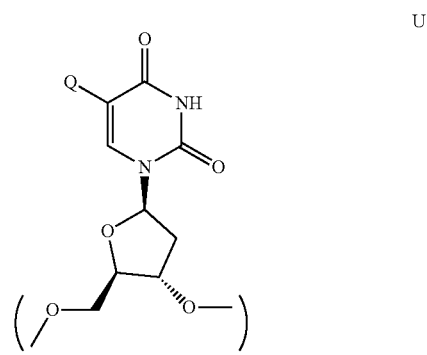

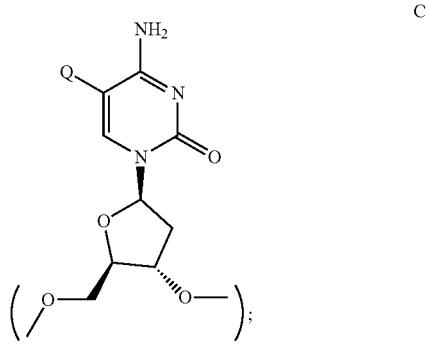

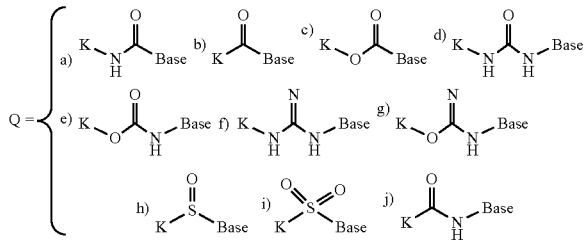

Base = Uridine (U) or Cytidine (C) (attachment is to the 5-position)
K = R' group plus (CH$_2$)$_n$ connecting group, where n = 0-3 wherein R' is defined as follows:

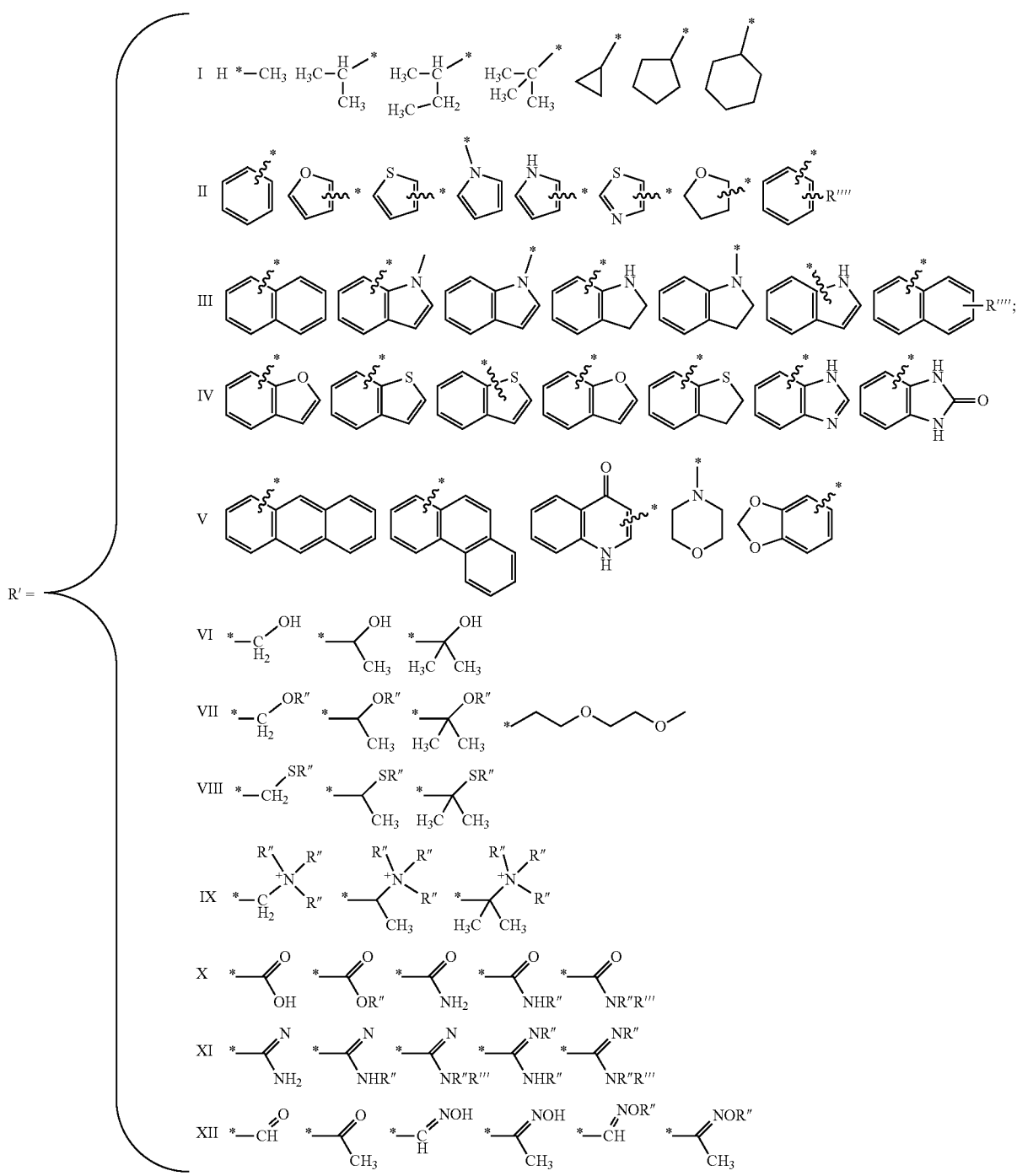

*Denotes point of attachment of the R' group to (CH2)n connecting group wherein
R"" is selected from the group consisting of a branched or linear lower alkyl (C1-C20); hydroxyl (OH), halogen (F, Cl, Br, I); nitrile (CN); boronic acid (BO₂H₂); carboxylic acid (COOH); carboxylic acid ester (COOR"); primary amide (CONH₂); secondary amide (CONHR"); tertiary amide (CONR"R'"); sulfonamide (SO₂NH₂); N-alkylsulfonamide (SONHR");

wherein
R", R'" are independently selected from a group consisting of a branched or linear lower alkyl (C1-C2)); phenyl (C6H5); an R"" substituted phenyl ring (R""C6H4); wherein R"" is defined above; a carboxylic acid (COOH); a carboxylic acid ester (COOR""); wherein R"" is a branched or linear lower alkyl (C1-C20); and cycloalkyl; wherein R"=R'"=(CH2)n;
wherein n=2-10.

In another aspect, W may represents a C-5 modified pyrimidine selected from the group consisting of 5-(N-benzylcarboxyamide)-2'-deoxyuridine (BndU), a 5-(N-isobutylcarboxyamide)-2'-deoxyuridine (iBudU), a 5-(N-tryptaminocarboxyamide)-2'-deoxyuridine (TrpdU), a 5-(N-naphthylmethylcarboxyamide)-2'-deoxyuridine (NapdU) and a combination thereof.

In another aspect, W represents a C-5 modified pyrimidine selected from the group consisting of a 5-(N-tryptaminocarboxyamide)-2'-deoxyuridine (TrpdU) and a 5-(N-naphthylmethylcarboxyamide)-2'-deoxyuridine (NapdU) and a combination thereof.

In another aspect, W may represent a compound comprising the structure shown in Formula I:

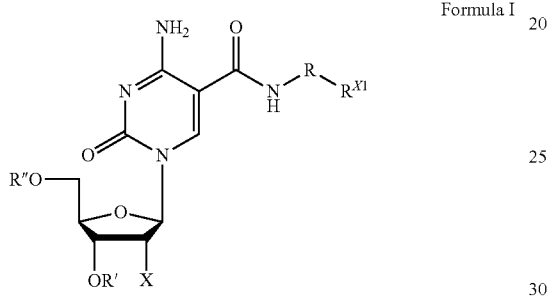

Formula I wherein
R is independently a —(CH$_2$)$_n$—, wherein n is an integer selected from 0, 1, 2, 3, 4, 5, 6, 7, 8, 9 or 10;
R$^{X1}$ is independently selected from the group consisting of:

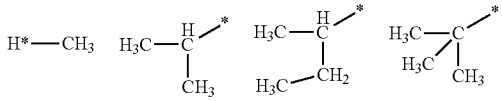

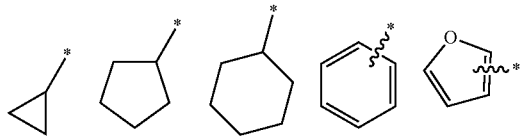

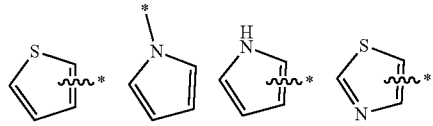

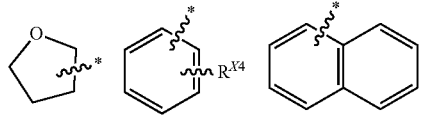

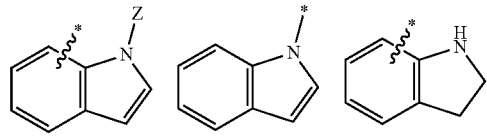

-continued

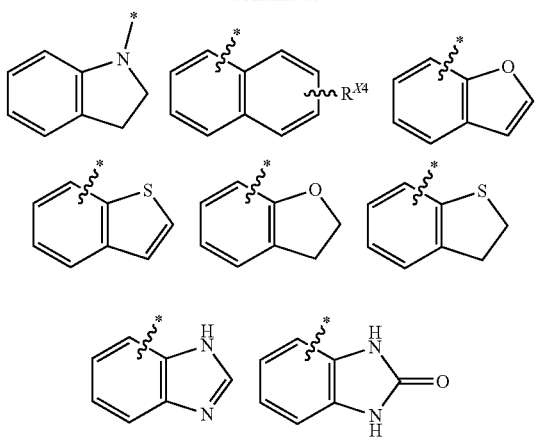

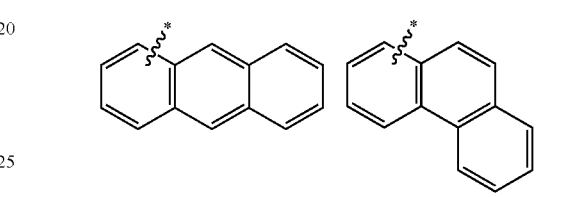

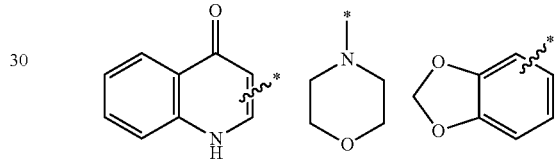

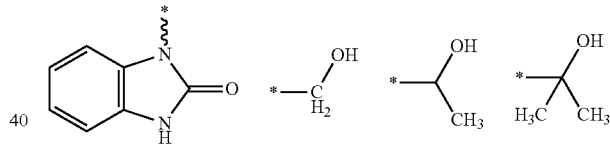

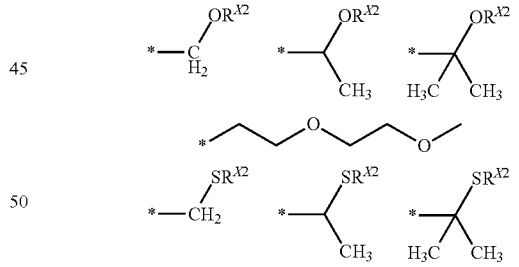

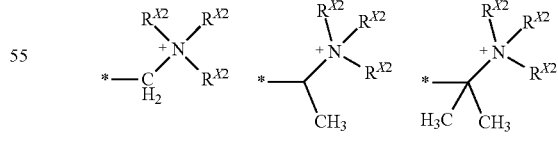

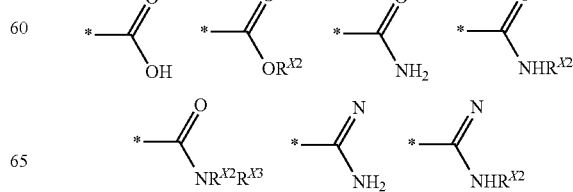

-continued

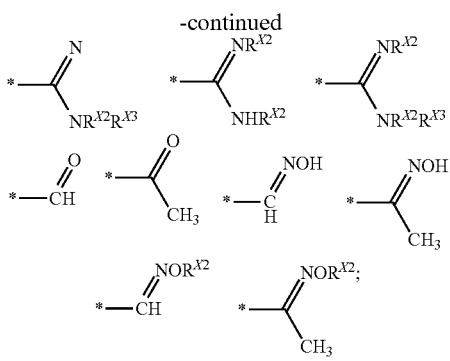

wherein * denotes the point of attachment of the $R^{X1}$ group to the —$(CH_2)_n$— group; and wherein
$R^{X4}$ is independently selected from the group consisting of a substituted or unsubstituted branched or linear lower alkyl (C1-C20); a hydroxyl group; a halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); N-alkylsulfonamide ($SONHR^{X2}$);
$R^{X2}$ and $R^{X3}$ are independently, for each occurrence, selected from the group consisting of a substituted or unsubstituted branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}$ and $R^{X3}$ together form a substituted or unsubstituted 5 or 6 membered ring;
X is independently selected from the group consisting of —H, —OH, —OMe, —O-allyl, —F, —OEt, —OPr, —$OCH_2CH_2OCH_3$, —$NH_2$ and -azido;
R' is independently selected from the group consisting of a —H, —OAc; —OBz; —$P(NiPr_2)(OCH_2CH_2CN)$; and —$OSiMe_2tBu$;
R" is independently selected from the group consisting of a hydrogen, 4,4'-dimethoxytrityl (DMT) and triphosphate (—P(O)(OH)—O—P(O)(OH)—O—P(O)$(OH)_2$) or a salt thereof;
Z is independently selected from the group consisting of a —H, a substituted or unsubstituted branched or linear lower alkyl (C1-C4);
and salts thereof;
with the following exceptions:
when n=4, then $R^{X1}$ cannot be H;
when n=3, then $R^{X1}$ cannot be $CH_3$;
when n=0, then $R^{X1}$ cannot be —$CH(CH_3)_2$; and
when n=2, and $R^{X1}$ is

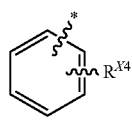

and $R^{X4}$ is hydroxyl then $R^{X1}$ cannot be

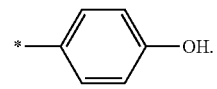

In related aspect n is an integer selected from 1, 2 or 3.
In related aspect, $R^{X1}$ is selected from the group consisting of:

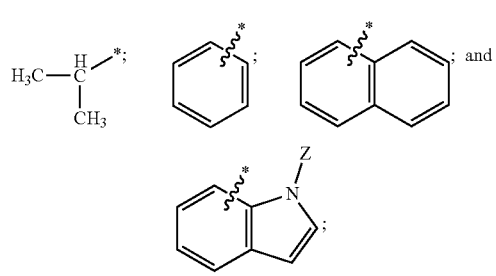

wherein
* denotes the point of attachment of the $R^{X1}$ group to the —$(CH_2)_n$— group; and
Z is independently selected from the group consisting of a —H, a substituted or unsubstituted branched or linear lower alkyl (C1-C4).

In related aspect, $R^{X4}$ is independently selected from the group consisting of a branched or linear lower alkyl (C1-C6); —OH; —F and carboxylic acid (COOH).

In related aspect, X is independently selected from the group consisting of —H, —OH, —OMe and —F.

In related aspect, R' is selected from the group consisting of a —H, —OAc and —$P(NiPr_2)(OCH_2CH_2CN)$.

In related aspect, R" is a triphosphate (—P(O)(OH)—O—P(O)(OH)—O—P(O)$(OH)_2$).

In another aspect, the disclosure provides for a compound comprising the structure selected from the group consisting of Formulas II (BndC), III (PEdC), IV (PPdC), V (NapdC), VI (2NapdC), VII (NEdC) and VIII (2NEdC):

Formula II

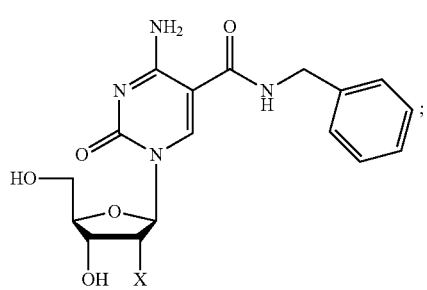

Formula III

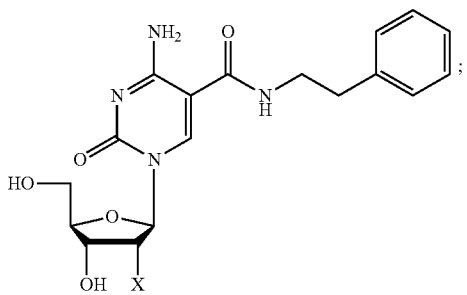

Formula IV

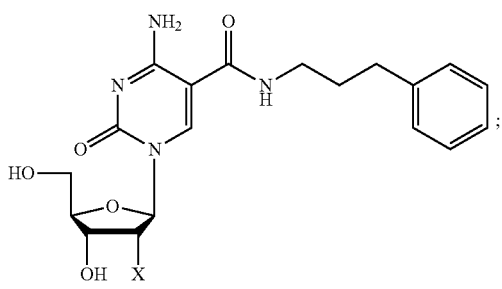

Formula V

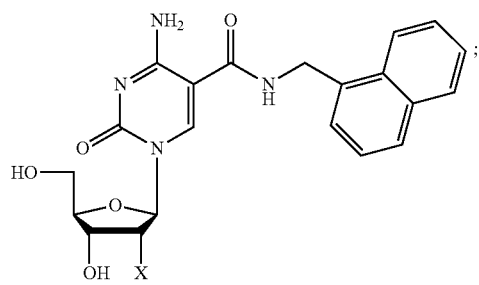

Formula VI

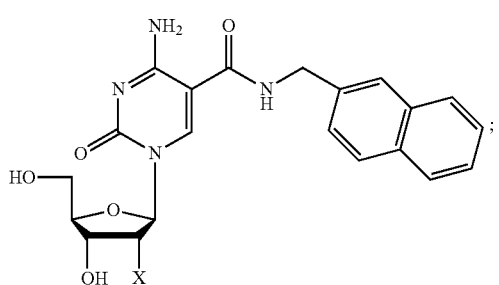

Formula VII

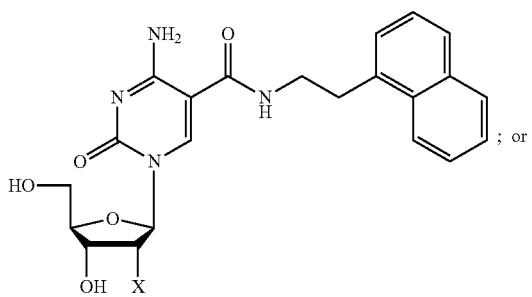

Formula VIII

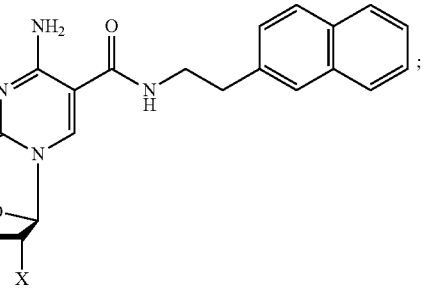

wherein
X is independently selected from the group consisting of —H, —OH, —OMe, —O-allyl, —F, —OEt, —OPr, —OCH$_2$CH$_2$OCH$_3$, —NH$_2$ and -azido.

In another aspect this disclosure, the aptamer may have a dissociation constant ($K_d$) for its target of about 10 nM or less. In another exemplary embodiment, the aptamer has a dissociation constant ($K_d$) for the target protein of about 15 nM or less. In yet another exemplary embodiment, the aptamer has a dissociation constant ($K_d$) for the target protein of about 20 nM or less. In yet another exemplary embodiment, the aptamer has a dissociation constant ($K_d$) for the target protein of about 25 nM or less. In yet another exemplary embodiment, the aptamer has a dissociation constant ($K_d$) for the target protein of about 30 nM or less. In yet another exemplary embodiment, the aptamer has a dissociation constant ($K_d$) for the target protein of about 35 nM or less. In yet another exemplary embodiment, the aptamer has a dissociation constant ($K_d$) for the target protein of about 40 nM or less. In yet another exemplary embodiment, the aptamer has a dissociation constant ($K_d$) for the target protein of about 45 nM or less. In yet another exemplary embodiment, the aptamer has a dissociation constant ($K_d$) for the target protein of about 50 nM or less. In yet another exemplary embodiment, the aptamer has a dissociation constant ($K_d$) for the target protein in a range of about 3-10 nM (or 3, 4, 5, 6, 7, 8, 9 or 10 nM0. A suitable dissociation constant can be determined with a binding assay using a multi-point titration and fitting the equation y=(max−min)(Protein)/($K_d$+Protein)+min. It is to be understood that the determination of dissociation constants is highly dependent upon the conditions under which they are measured and thus these numbers may vary significantly with respect to factors such as equilibration time, etc. In other embodiments, the aptamer has a $K_d$ that is less than or equal to the $K_d$ of an aptamer selected from SEQ ID NOS: 1-15.

The motif for the aptamer sequence that binds the ClfA protein is represented by SEQ ID NO: 13. This sequence motif may be further generalized to the following sequence:

(SEQ ID NO: 15)
AWCWGGWWC(N)$_n$AWCWGGWWWWWAAG

The "W" in the sequence represents a position that may be occupied by a C-5 modified pyrimidine, and "N" represents a position that may be occupied by any unmodified or modified nucleotide or a spacer-sequence or linker. Further, n may be a number from 1 to 30 (or 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30), or from 2 to 20 (or 2, 3, 4, 5, 6, 7, 8, 9, 10, 11, 12, 13, 14, 15, 16, 17, 18, 19 or 20), or from 5 to 18 (or 5, 6, 7, 8, 9, 10, 11, 12, 13, 14, 15, 16, 17 or 18), or from 10 to 16 (or 10, 11, 12, 13, 14, 15 or 16), or N is about 16.

In another aspect, the nucleotide sequence may include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

In another aspect this disclosure, the aptamer may be at least about 95% identical, at least about 90% identical, at least about 85% identical, at least about 80% identical, or at least about 75% identical to any of SEQ ID NO:15. In another embodiment, the aptamer includes a sequence fragments of SEQ ID NO:15.

In another aspect, the aptamer comprises from about 1% to 100% (or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%) C-5 modified pyrimidines. In another aspect, the aptamer comprises from about 10% to about 50% (or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50%) C-5 modified pyrimidines. In another aspect, the aptamer comprises, from about 20% to about 40% (or 20, 21, 22, 23, 24, 25, 26, 27, 28, 29, 30, 31, 32, 33, 34, 35, 36, 37, 38, 39 or 40%) C-5 modified pyrimidines. In another aspect, the aptamer comprises from about 25% to about 35% (or 25, 26, 27, 28, 29, 30, 31, 32, 33, 34, 35%) C-5 modified pyrimidines. In another aspect, the aptamer comprises from about 27% to about 33% (or 27, 28, 29, 30, 31, 32 or 33%) C-5 modified pyrimidines. In another aspect, the aptamer comprises from about 37% to about 43% (or 37, 38, 39, 40, 41, 42, 43%) C-5 modified pyrimidines.

In another aspect, the W may represent a C-5 modified uridine or cytidine.

In another aspect, the W may represent a C-5 modified pyrimidine illustrated immediately below:

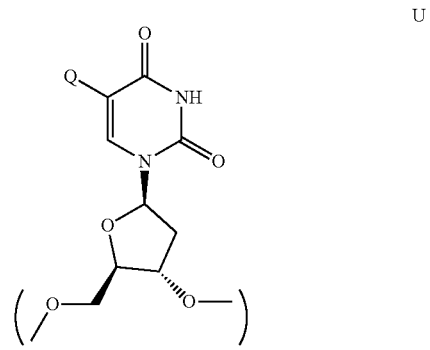

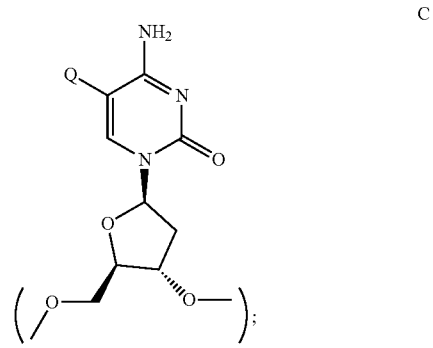

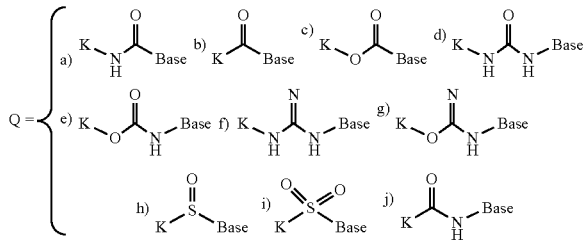

Base = Uridine (U) or Cytidine (C) (attachment is to the 5-position)
K = R' group plus (CH$_2$)$_n$ connecting group, where n = 0-3 wherein R' is defined as follows:

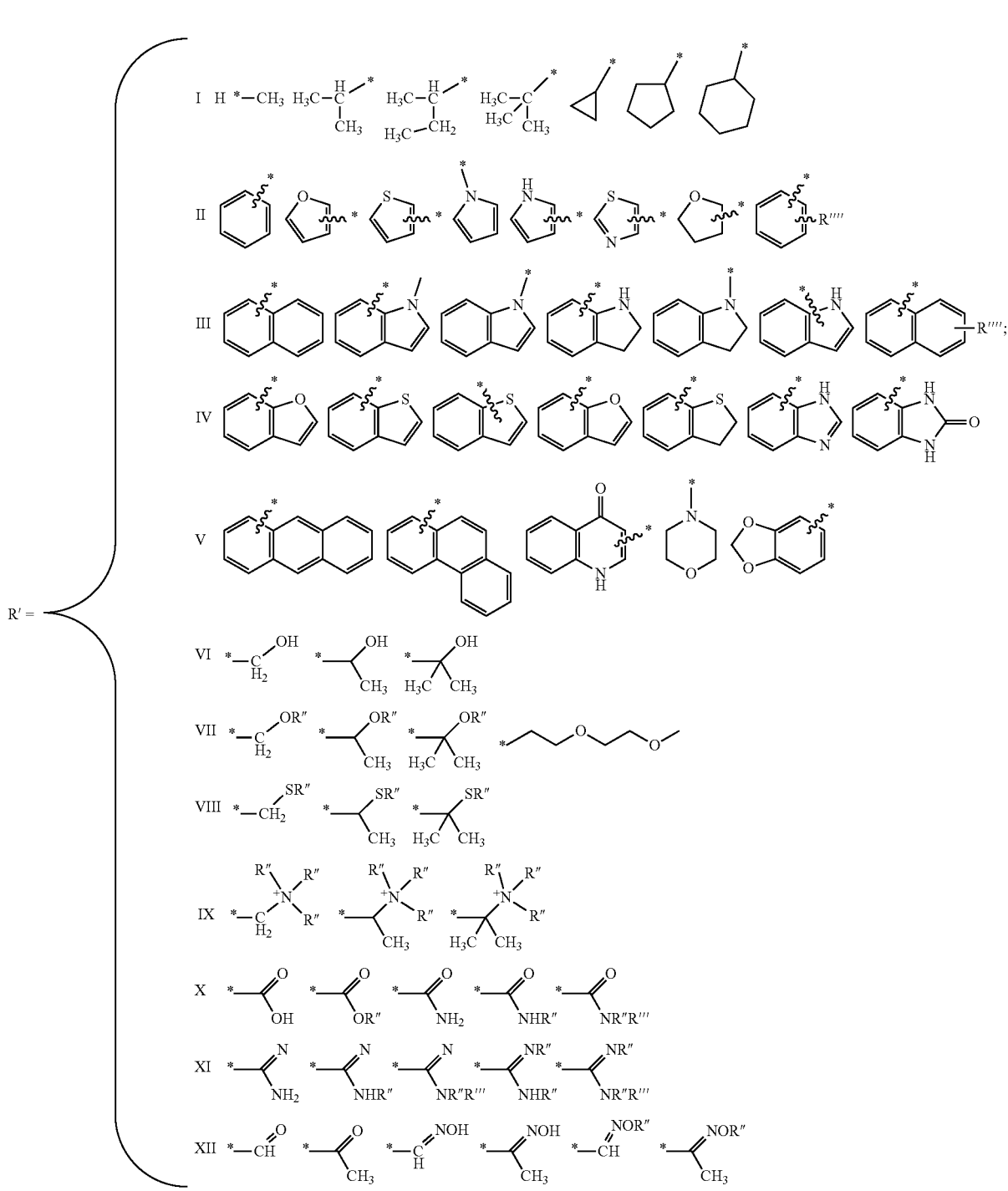

*Denotes point of attachment of the R' group to (CH2)n connecting group wherein
R"" is selected from the group consisting of a branched or linear lower alkyl (C1-C20); hydroxyl (OH), halogen (F, Cl, Br, I); nitrile (CN); boronic acid (BO₂H₂); carboxylic acid (COOH); carboxylic acid ester (COOR"); primary amide (CONH₂); secondary amide (CONHR"); tertiary amide (CONR"R'"); sulfonamide (SO₂NH₂); N-alkylsulfonamide (SONHR");

wherein
R", R'" are independently selected from a group consisting of a branched or linear lower alkyl (C1-C2)); phenyl (C6H5); an R"" substituted phenyl ring (R""C6H4); wherein R"" is defined above; a carboxylic acid (COOH); a carboxylic acid ester (COOR""); wherein R"" is a branched or linear lower alkyl (C1-C20); and cycloalkyl; wherein R"=R'"=(CH2)n;
wherein n=2-10.

In another aspect, the W may represent a C-5 modified pyrimidine selected from the group consisting of 5-(N-benzylcarboxyamide)-2'-deoxyuridine (BndU), a 5-(N-isobutylcarboxyamide)-2'-deoxyuridine (iBudU), a 5-(N-tryptaminocarboxyamide)-2'-deoxyuridine (TrpdU), a 5-(N-naphthylmethylcarboxyamide)-2'-deoxyuridine (NapdU) and a combination thereof.

In another aspect, the W may represents a C-5 modified pyrimidine selected from the group consisting of a 5-(N-tryptaminocarboxyamide)-2'-deoxyuridine (TrpdU) and a 5-(N-naphthylmethylcarboxyamide)-2'-deoxyuridine (NapdU) and a combination thereof. In another aspect, the W may represent a compound comprising the structure shown in Formula I:

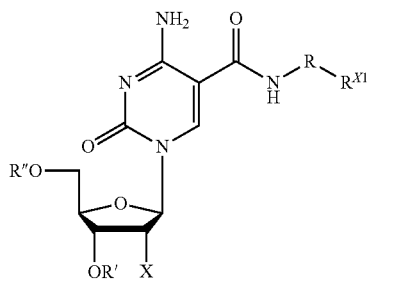

Formula I wherein

R is independently a —(CH$_2$)$_n$—, wherein n is an integer selected from 0, 1, 2, 3, 4, 5, 6, 7, 8, 9 or 10;

R$^{X1}$ is independently selected from the group consisting of:

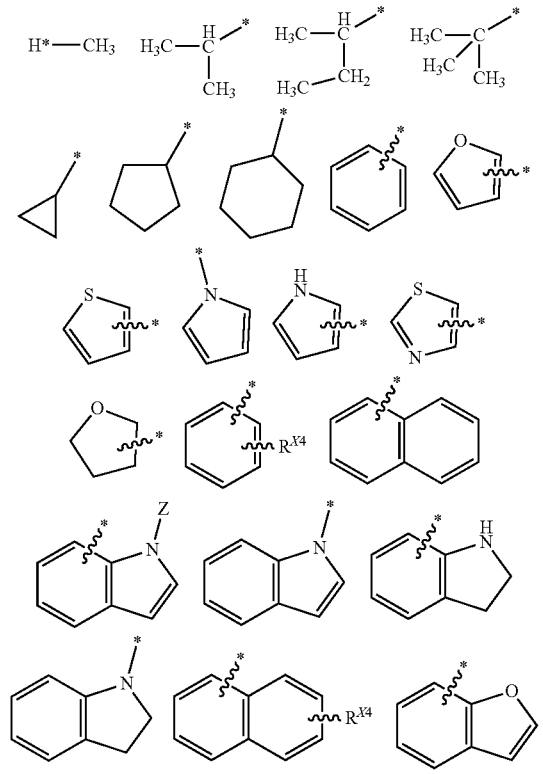

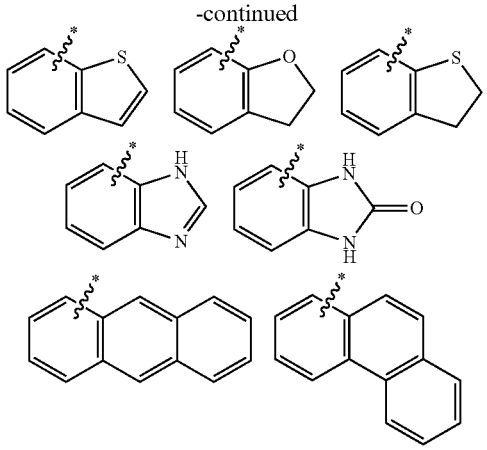

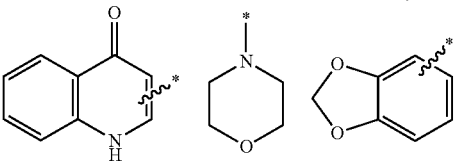

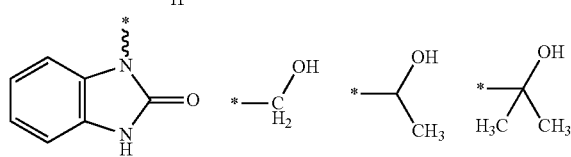

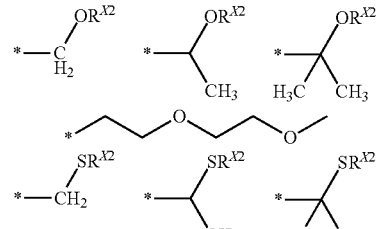

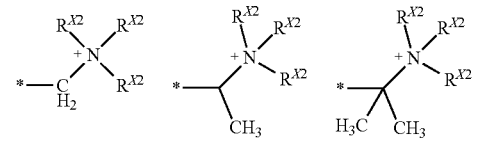

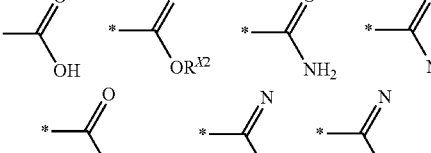

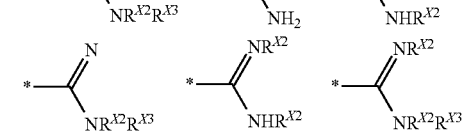

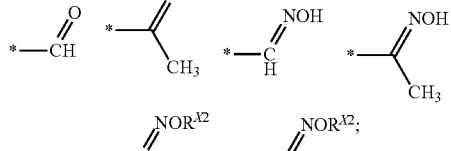

wherein * denotes the point of attachment of the R$^{X1}$ group to the —(CH$_2$)$_n$— group; and wherein $R^{X4}$ is independently selected from the group consisting of a substituted or unsubstituted branched or linear lower alkyl (C1-C20); a hydroxyl group; a halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); N-alkylsulfonamide ($SONHR^{X2}$);

$R^{X2}$ and $R^{X3}$ are independently, for each occurrence, selected from the group consisting of a substituted or unsubstituted branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}$ and $R^{X3}$ together form a substituted or unsubstituted 5 or 6 membered ring;

X is independently selected from the group consisting of —H, —OH, —OMe, —O-allyl, —F, —OEt, —OPr, —$OCH_2CH_2OCH_3$, —$NH_2$ and -azido;

R' is independently selected from the group consisting of a —H, —OAc; —OBz; —$P(NiPr_2)(OCH_2CH_2CN)$; and —$OSiMe_2tBu$;

R" is independently selected from the group consisting of a hydrogen, 4,4'-dimethoxytrityl (DMT) and triphosphate (—P(O)(OH)—O—P(O)(OH)—O—$P(O)(OH)_2$) or a salt thereof;

Z is independently selected from the group consisting of a —H, a substituted or unsubstituted branched or linear lower alkyl (C1-C4);

and salts thereof;
with the following exceptions:
when n=4, then $R^{X1}$ cannot be H;
when n=3, then $R^{X1}$ cannot be $CH_3$;
when n=0, then $R^{X1}$ cannot be —$CH(CH_3)_2$; and when n=2, and $R^{X1}$ is

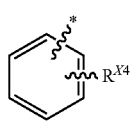

and $R^{X4}$ is hydroxyl then $R^{X1}$ cannot be

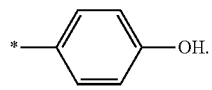

In related aspect n is an integer selected from 1, 2 or 3.
In related aspect, $R^{X1}$ is selected from the group consisting of:

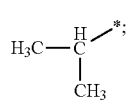  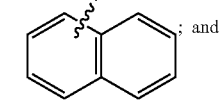 ; and

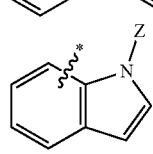

wherein
* denotes the point of attachment of the $R^{X1}$ group to the —$(CH_2)_n$— group; and
Z is independently selected from the group consisting of a —H, a substituted or unsubstituted branched or linear lower alkyl (C1-C4).

In related aspect, $R^{X4}$ is independently selected from the group consisting of a branched or linear lower alkyl (C1-C6); —OH; —F and carboxylic acid (COOH).

In related aspect, X is independently selected from the group consisting of —H, —OH, —OMe and —F.

In related aspect, R' is selected from the group consisting of a —H, —OAc and —$P(NiPr_2)(OCH_2CH_2CN)$.

In related aspect, R" is a triphosphate (—P(O)(OH)—O—P(O)(OH)—O—$P(O)(OH)_2$).

In another aspect, the disclosure provides for a compound comprising the structure selected from the group consisting of Formulas II (BndC), III (PEdC), IV (PPdC), V (NapdC), VI (2NapdC), VII (NEdC) and VIII (2NEdC):

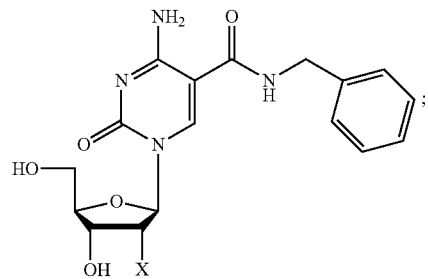

Formula II

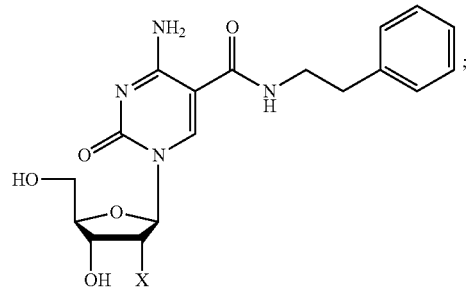

Formula III

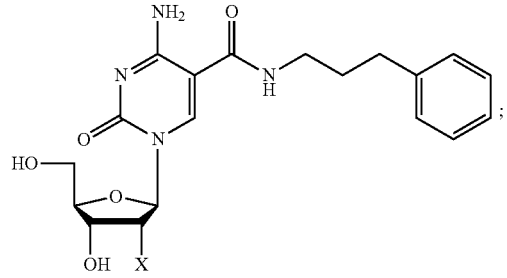

Formula IV

Formula V

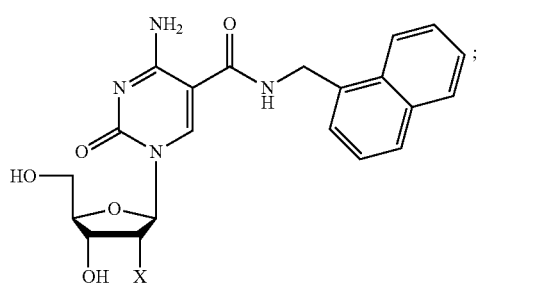

Formula VI

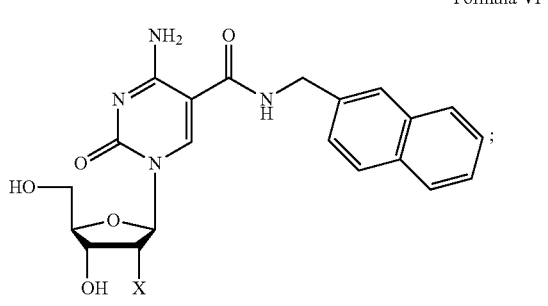

Formula VII

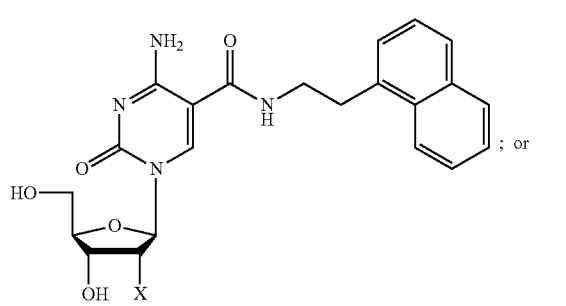

Formula VIII

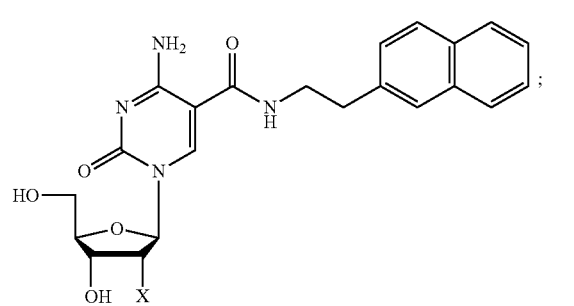

wherein
X is independently selected from the group consisting of —H, —OH, —OMe, —O-allyl, —F, —OEt, —OPr, —OCH$_2$CH$_2$OCH$_3$, —NH$_2$ and -azido.

In another aspect this disclosure, the aptamer may have a dissociation constant (K$_d$) for its target of about 10 nM or less. In another exemplary embodiment, the aptamer has a dissociation constant (K$_d$) for the target protein of about 15 nM or less. In yet another exemplary embodiment, the aptamer has a dissociation constant (K$_d$) for the target protein of about 20 nM or less. In yet another exemplary embodiment, the aptamer has a dissociation constant (K$_d$) for the target protein of about 25 nM or less. In yet another exemplary embodiment, the aptamer has a dissociation constant (K$_d$) for the target protein of about 30 nM or less. In yet another exemplary embodiment, the aptamer has a dissociation constant (K$_d$) for the target protein of about 35 nM or less. In yet another exemplary embodiment, the aptamer has a dissociation constant (K$_d$) for the target protein of about 40 nM or less. In yet another exemplary embodiment, the aptamer has a dissociation constant (K$_d$) for the target protein of about 45 nM or less. In yet another exemplary embodiment, the aptamer has a dissociation constant (K$_d$) for the target protein of about 50 nM or less. In yet another exemplary embodiment, the aptamer has a dissociation constant (K$_d$) for the target protein in a range of about 3-10 nM (or 3, 4, 5, 6, 7, 8, 9 or 10 nM0. A suitable dissociation constant can be determined with a binding assay using a multi-point titration and fitting the equation y=(max−min)(Protein)/(K$_d$+Protein)+min. It is to be understood that the determination of dissociation constants is highly dependent upon the conditions under which they are measured and thus these numbers may vary significantly with respect to factors such as equilibration time, etc. In other embodiments, the aptamer has a K$_d$ that is less than or equal to the K$_d$ of an aptamer selected from SEQ ID NOS: 1-15.

The present disclosure further provides a method for detecting the presence or absence of a microorganism in a sample comprising: contacting the sample with an aptamer and performing an assay to detect the aptamer, wherein detecting the second aptamer indicates that the microorganism is present in the sample, and wherein not detecting the second aptamer indicates that the microorganism is absent from the sample; wherein, the aptamer comprises a nucleic acid molecule having the sequence selected from the group consisting of GGCWWCGGGWACCWAWWAWNGGW-WWAGCC(N)$_x$GWC (SEQ ID NO:14) and AWCWGGW-WC(N)$_y$WCWGGWWWWWAAG (SEQ ID NO:15), and wherein W is independently, for each occurrence, a C-5 modified pyrimidine, N is any unmodified or modified nucleotide, and x is 0, 1, 2, 3, 4 or 5, and y is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In another aspect, the C-5 modified pyrimidine is selected from the group consisting of 5-(N-benzylcarboxyamide)-2'-deoxycytidine (BndC); 5-(N-2-phenylethylcarboxyamide)-2'-deoxycytidine (PEdC); 5-(N-3-phenylpropylcarboxyamide)-2'-deoxycytidine (PPdC); 5-(N-1-naphthylmethylcarboxyamide)-2'-deoxycytidine (NapdC); 5-(N-2-naphthylmethylcarboxyamide)-2'-deoxycytidine (2NapdC); 5-(N-1-naphthyl-2-ethylcarboxyamide)-2'-deoxycytidine (NEdC); 5-(N-2-naphthyl-2-ethylcarboxyamide)-2'-deoxycytidine (2NEdC); 5-(N-benzylcarboxyamide)-2'-deoxyuridine (BndU); 5-(N-isobutylcarboxyamide)-2'-deoxyuridine (iBudU); 5-(N-tryptaminocarboxyamide)-2'-deoxyuridine (TrpdU); 5-(N-[1-(3-trimethylamonium) propyl]carboxyamide)-2'-deoxyuridine chloride and 5-(N-naphthylmethylcarboxyamide)-2'-deoxyuridine (NapdU).

In another aspect, the aptamer is amplifiable.

In another aspect, the assay is selected from the group consisting of PCR, qPCR, mass spectroscopy, sequencing and hybridization.

In another aspect, the microorganism is selected from the group consisting of a bacterial cell, parasite and virus. In a related aspect, the microorganism is a bacterial cell. In yet another related aspect, the bacterial cell is pathogenic.

In another aspect, the bacterial cell is a *Staphylococcus* cell.

In another aspect, the bacterial cell is a *Staphylococcus aureus* cell.

In another aspect, the aptamer comprises a nucleic acid molecule having a sequence selected from the group consisting of SEQ ID NOs: 1-8 and 10-12, wherein W is a C-5 modified pyrimidine.

In another aspect, the disclosure provides a composition comprising SEQ ID NOs: 1-15.

The following examples are provided to illustrate certain particular features and/or embodiments. These examples should not be construed to limit the disclosure to the particular features or embodiments described.

EXAMPLES

Example 1: Selection and Identification of Aptamers Having Binding Specificity to S. aureus Proteins This example provides the representative method for the selection and production of aptamers having binding specificity to the following ten surface-associated S. aureus proteins: SpA, ClfA, ClfB, FnbA, FnbB, SasD, IsdA, IsdB, IsdC and IsdH.

Purification of S. aureus Targets

Relevant portions of the genes encoding the desired targets or target domains were PCR-amplified from S. aureus NRS384 (USA300) genomic DNA with primers and cloned into pCR-Script SK+ (Stratgene). The clfA, clfB, fnbA, sasD, isdA, isdB, isdC, and isdH genes were transferred as BamHI-SacI cassettes into the expression vector pET-51b (EMD-Novagen) that harbors an aminoterminal Strep-tag and a carboxyterminal $His_{10}$-tag. One of the targets, fnbB, was cloned as and NdeI-BamHI fragment into pET-14b (EMD-Novagen), which harbors an amino-terminal $His_{10}$-tag. The plasmids were sequenced to verify the gene identity and proper gene fusion of the cloned DNA fragment with the vector-encoded sequences for the His-tag and Strep tag.

The recombinant proteins were over-expressed in E. coli BL21(DE3) or in BL21(DE3)/pLysE (EMD/Novagen). Conditions for optimal expression of soluble proteins were optimized with respect to growth temperature (25-37° C.) and induction time (4-15 h). Cells from 0.1-0.8 l cultures were lysed with 10 ml BugBuster/Benzonase reagent (EMD Millipore). The recombinant, $His_{10}$/Strep-tagged proteins were purified from the soluble fraction via sequential affinity chromatography on Ni-NTA agarose and Strep•Tactin® Superflow™ agarose (EMD Millipore). Native staphylococcal protein A was purchased from VWR and was biotinylated with NHS-PEG4-biotin (Pierce Biotechnology). Protein concentrations were determined using the Quick Start Bradford Protein Assay Kit (BioRad).

Figure 3:
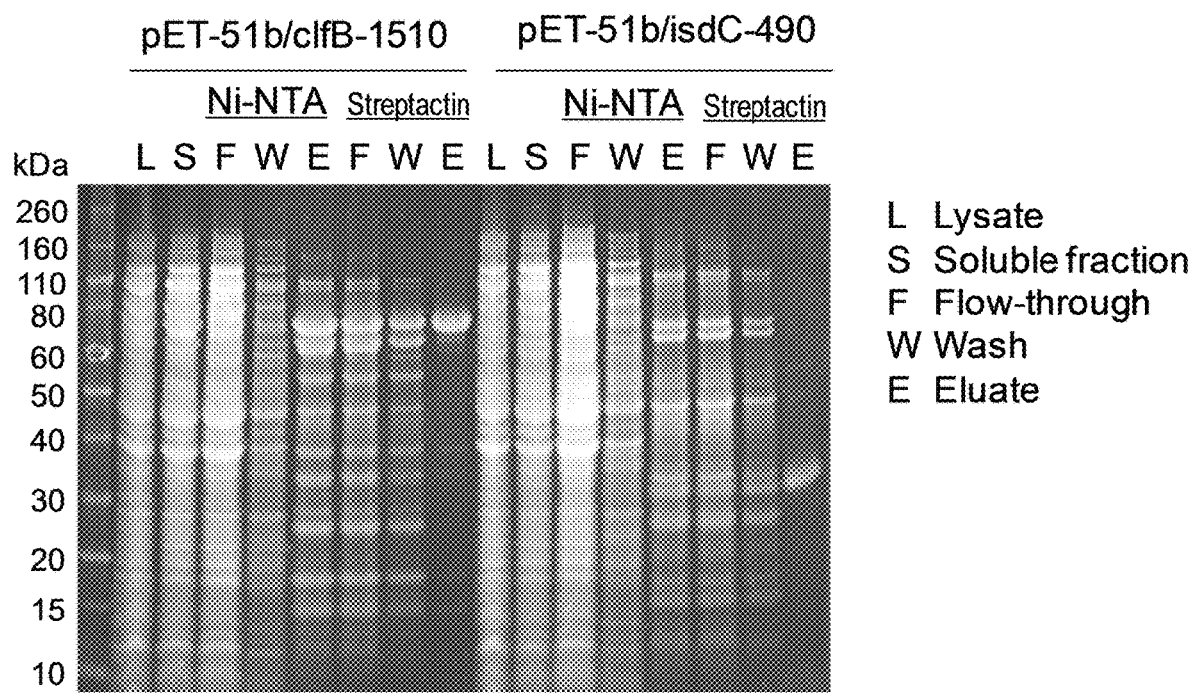
FIG. 3 shows an SDS-PAGE analysis of cell surface-associated *S. aureus* proteins over-expressed in recombinant form in *E. coli* and purified by affinity chromatography on Ni-NTA agarose and Streptactin Sepharose.

All 10 recombinant S. aureus cell surface proteins were found in the soluble fraction when over-expressed in E. coli. Sequential affinity chromatography on Ni-NTA agarose and Streptactin Sepharose yielded 0.1-1.5 mg of each protein in >95% purity (see FIG. 3).

Aptamer Selection

Separate libraries with 5-(N-benzylcarboxyamide)-dU (BndU), 5-(N-naphthylmethylcarboxyamide)-dU (NapdU), and 5-(N-tryptaminocarboxyamide)-dU (TrpdU) were used for SELEX with the S. aureus proteins. Each selection started from 1 nmol ($10^{14}$-$10^{15}$) sequences containing 40 consecutive randomized positions flanked by fixed sequences required for PCR amplification. SELEX was performed essentially as described (Gold et al., 2010; Vaught et al., 2010; Ochsner et al., 2013). Buffer SB18T was used through-out SELEX and subsequent binding assays, consisting of 40 mmol $l^{-1}$ HEPES pH 7.5, 0.1 mol $l^{-1}$ NaCl, 5 mmol $l^{-1}$ KCl, 5 mmol $l^{-1}$ $MgCl_2$, and 0.05% Tween-20. Eight rounds of selection were carried out, and, beginning with round 2, a kinetic challenge with 10 mmol $l^{-1}$ dextran sulfate was performed to favor slow off-rates. Partitioning of the aptamer-target complexes was achieved with paramagnetic Talon Dynabeads® Talon® (Invitrogen) that bind the $His_{10}$-tag on the recombinant proteins, or with MyOne Streptavidin C1 beads (Life Technologies) for the biotinylated SPA. Selected sequences were eluted from the bead-bound targets with 80 µl 40 mmol $l^{-1}$ NaOH, neutralized with 20 µl of 160 mmol $l^{-1}$ HCl, and PCR-amplified using KOD EX DNA polymerase (Invitrogen-Life Technologies). Modified DNA for the next round was prepared with KOD EX DNA polymerase via primer extension from the antisense strand of the PCR products and purified as described (Gold et al., 2010).

DNA reassociation kinetic analysis (Cot) of selected DNA from rounds 3 through 8 was used for the assessment of sequence convergence during the later rounds, indicating increased abundance of some sequences or sequence families. Aptamer pools that demonstrated good affinity ($K_d \leq 10$ nmol $l^{-1}$) in solution binding radioassays (see below) were cloned and the sequences of 48 clones per pool were determined. Up to 12 individual aptamers were chosen based on sequence patterns and diversity and prepared enzymatically for further characterization.

Synthetic aptamers were prepared as 48-50-mers at 1 µmol scale via standard phosphoramidite chemistry and HPLC purified. They contained a 5'biotin-dA or 5'fluorescein-biotin-dA, and an inverted dT nucleotide at the 3' end (3'idT) for added stability to 3' to 5' exonucleases.

Eight rounds of SELEX were performed with these proteins, using three separate ssDNA libraries, and Cot reassociation kinetics indicated a reduction of sequence complexity. Pool affinity assays confirmed the successful selection of aptamers for a total of 22 pools obtained with the ssDNA C-5 modified nucleotides BndU, NapdU, or TrpdU, with pool affinities in the range of 0.13-8.90 nmol $l^{-1}$. Specific binding to S. aureus cells, but no binding to S. epidermidis, S. haemolyticus, S. pyogenes, E. faecalis, E. coli, or P. aeruginosa was observed.

Alignment of sequences determined for 48 clones from each pool showed multi-copy clones and families that shared common sequence patterns. Representative clones were screened in affinity assays, and the $K_d$'s of the aptamers were in the range of 0.03-2.17 nmol $l^{-1}$ (Table 1).

TABLE 1

Aptamer for S. aureus cell surface proteins, with affinity ($K_d$) shown for the original full-length sequences obtained in SELEX

| | Aptamer Characterization | | | | | |
|---|---|---|---|---|---|---|
| Protein Target | Clone Identifier | C-5 Mod. | $K_d$ (nmol $l^{-1}$) | Nt. Length | No. of C-5 Mods. | % C-5 Mods. |
| SPA | 4520-8 | NapdU | 0.22 | 40 | 12 | 30% |
| | 4531-56 | TrpdU | 0.03 | 39 | 12 | 30.8% |
| ClfA | 4503-73 | BndU | 0.79 | 40 | 15 | 37.5% |
| | 4522-5 | TrpdU | 0.35 | 39 | 12 | 30.8% |
| ClfB | 4504-27 | BndU | 1.35 | 40 | 19 | 47.5% |
| | 4511-67 | NapdU | 3.90 | 40 | 16 | 40% |
| | 4523-79 | TrpdU | 0.47 | 40 | 13 | 32.5% |
| FnbA | 4726-44 | NapdU | 4.38 | 40 | 8 | 20% |
| | 4745-51 | TrpdU | 0.63 | 40 | 10 | 25% |
| FnbB | 4506-13 | BndU | 4.73 | 39 | 21 | 52.5% |
| | 4516-29 | NapdU | 0.63 | 40 | 11 | 27.5% |
| | 4527-83 | TrpdU | 0.84 | 40 | 13 | 32.5% |

TABLE 1-continued

Aptamer for *S. aureus* cell surface proteins, with affinity ($K_d$) shown for the original full-length sequences obtained in SELEX Aptamer Characterization

| Protein Target | Clone Identifier | C-5 Mod. | $K_d$ (nmol l$^{-1}$) | Nt. Length | No. of C-5 Mods. | % C-5 Mods. |
|---|---|---|---|---|---|---|
| IsdA | 4727-62 | NapdU | 0.73 | 40 | 11 | 27.5% |
|  | 4746-3 | TrpdU | 0.16 | 40 | 12 | 30% |
| IsdB | 4728-7 | NapdU | 0.14 | 40 | 9 | 22.5% |
|  | 4747-90 | TrpdU | 1.98 | 40 | 9 | 22.5% |
| IsdC | 4507-52 | BndU | 0.15 | 40 | 18 | 45% |
|  | 4517-71 | NapdU | 0.08 | 40 | 12 | 30% |
|  | 4528-22 | TrpdU | 0.07 | 40 | 14 | 35% |
| IsdH | 4731-69 | NapdU | 1.30 | 40 | 11 | 27.5% |
| SasD | 4730-3 | NapdU | 2.17 | 40 | 10 | 25% |

The aptamers of Table 1, generally, are from 39 to 40 nucleotides in length and comprise a C-5 modified pyrimidine (e.g., BndU, TrpdU or a NapdU). Further, the aptamers of able 1 comprise from about 8 to about 21 C-5 modified pyrimidines (8, 9, 10, 11, 12, 13, 14, 15, 16, 18, 19 or 21 C-5 modified pyrimidines), or from about 20% C-5 modified pyrimidines to about 53% C-5 modified pyrimidines (or from 20%, 22.5%, 25%, 27.5%, 30%, 30.8%, 32.5%, 35%, 37.5%, 40%, 45%, 47.5% or 52.5%). The aptamers of table 1, generally, have a $K_d$ of from about 0.03 nM to about 4.7 nM (or 0.03, 0.07, 0.08, 0.14, 0.15, 0.16, 0.22, 0.35, 0.47, 0.63, 0.73, 0.79, 0.84, 1.3, 1.35, 1.98, 2.17, 3.9 and 4.73 nM).

The nucleotide sequence of selected clones that target the SPA protein and separately the ClfA protein are identified in Table 2 below.

TABLE 2

Select Aptamer Nucleotide Sequences of Aptamers Identified via SELEX

| Target | Clone Ident. | SEQ ID NO: | Nucleotide Sequence (5' to 3') |
|---|---|---|---|
| SPA* | 4520-3 | 1 | CCGGCWWCGGGWACCWAWWAWCGGWWWAGCCCAGWCATAA |
|  | 4520-8 | 2 | WCGGCWWCGGGWACCWAWWAWCGGWWWAGCCCAGWCAGAA |
|  | 4520-20 | 3 | GCGGCWWCGGGWACCWAWWAWCGGWWWAGCCCAGWCAAAA |
|  | 4520-23 | 4 | GWGGCWWCGGGWACCWAWWAWCGGWWWAGCCCAGWCAGAA |
|  | 4520-27 | 5 | GCGGCWWCGGGWACCWAWWAWCGGWWWAGCCCWGWCAGGA |
|  | 4520-30 | 6 | CGAGCGGCWWCGGGWACCWAWWAWGGWWWAGCCCAGWCAGAA |
|  | 4520-42 | 7 | WCGGCWWCGGGWACCWAWWAWCGGWWWAGCCCAGWCWGAA |
|  | 4520-44 | 8 | ACGGCWWCGGGWACCWAWWAWCGGWWWAGCC-AGWCAGAA |
|  | SPA Seq. Motif | 9 | GGCWWCGGGWACCWAWWAW-GGWWWAGCC--GWC |
| ClfA+ | 4503-66 | 10 | AWCWGGWWCAAAGWGACGAWWGGGCAWCWGGWWWWWAAGW |
|  | 4503-68 | 11 | AWCWGGWWCWAAGWWACWWGGCGWAAWCWGGWWWWWAAGA |
|  | 4503-73 | 12 | AWCWGGWWCAAAGWGGCGAWWGGGCAWCWGGWWWWWAAGW |
|  | ClfA Seq. Motif | 13 | AWCWGGWWC---------------AWCWGGWWWWWAAG |

*indicates that the nucleotide "W" in the sequences that target the SPA protein are a C-5 modified nucleotide (specifically a NapdU)
+indicates that the nucleotide "W" in the sequences that target the ClfA protein are a C-5 modified nucleotide (specifically a BndU)

The motif (4520) for the aptamer sequence that binds the SPA protein is represented by SEQ ID NO:9. This sequence motif may be further generalized to the following sequence:

(SEQ ID NO: 14)
GGCWWCGGGWACCWAWWAWNGGWWWAGCC(N)$_n$GWC.

The "W" in the sequence represents a position that may be occupied by a C-5 modified pyrimidine, and "N" represents a position that may be occupied by any unmodified or modified nucleotide, and n is from 0 to 2 (or 0, 1 or 2).

The motif (4503) for the aptamer sequence that binds the ClfA protein is represented by SEQ ID NO:13. This sequence motif may be further generalized to the following sequence:

(SEQ ID NO: 15)
AWCWGGWWC(N)$_n$AWCWGGWWWWWAAG

The "W" in the sequence represents a position that may be occupied by a C-5 modified pyrimidine, and "N" represents a position that may be occupied by any unmodified or modified nucleotide. Further, n may be a number from 1 to 30 (or 1, 2, 3, 4, 5, 6, 7, 8, 9, 10, 11, 12, 13, 14, 15, 16, 17, 18, 19, 20, 21, 22, 23, 24, 25, 26, 27, 28, 29 or), or from 2 to 20 (or 2, 3, 4, 5, 6, 7, 8, 9, 10, 11, 12, 13, 14, 15, 16, 17, 18, 19 or 20), or from 5 to 18 (or 5, 6, 7, 8, 9, 10, 11, 12, 13, 14, 15, 16, 17 or 18), or from 10 to 16 (or 10, 11, 12, 13, 14, 15 or 16).

Example 2: Binding and Selective Capture of Bacterial Cells by Aptamers

This example shows that the aptamers selected and identified to bind *S. aureus* cell surface proteins also bind whole cells and are capable of selectively capturing *S. aureus* cells in a mixed bacterial culture Aptamer Equilibrium and Whole Cell Radiolabel Binding Assays Aptamers were properly folded via heating for 5 min at 95° C., followed by cooling to room temperature over a 10-15 min period, prior to binding assays.

Affinities ($K_d$'s) were determined in equilibrium solution binding assays of radiolabeled aptamers (10-20 μmol l$^{-1}$) with serially diluted proteins (0.001-100 nmol l$^{-1}$) and Zorbax PSM-300A (Agilent Technologies) resin for partitioning onto filter plates as described (Gold et al. 2010).

Prior to cloning, the aptamer pools were also tested for specific binding to *S. aureus*, using *S. epidermidis*, *S. haemolyticus*, *Strep. pyogenes*, *Ent. faecalis*, *E. coli*, and *Ps. aeruginosa* as controls in 2 h equilibrium binding assays. Cell densities ranged from 10$^5$-10$^8$ CFU mL$^{-1}$, and 0.1 mmol l$^{-1}$ dextran sulfate and 0.35 mol l$^{-1}$ NaCl was added to the binding buffer to reduce non-specific background. In addition, individual aptamers were screened for binding to eight different *S. aureus* strains belonging to different lineages, including NRS382, NRS383, NRS384, NRS123, NRS385, NRS386, NRS103 (NARSA), and ATCC 29213 (ATCC).

Figure 4A:
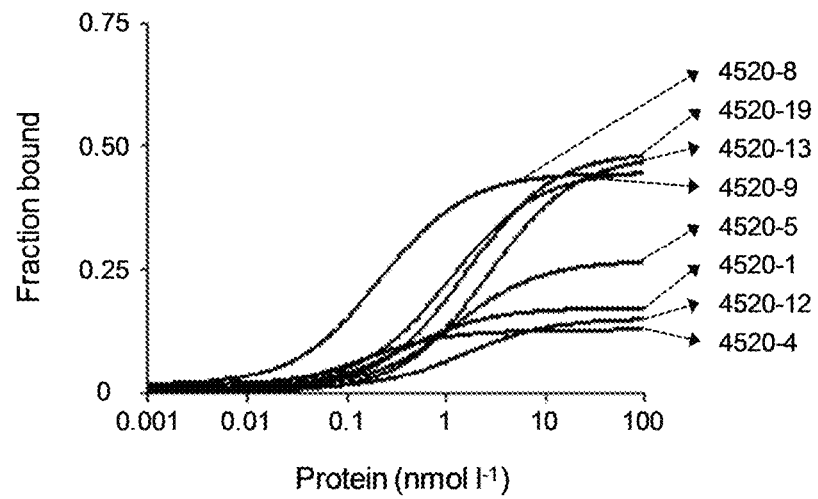
FIGS. 4A-B show a radiolabel affinity binding assays with individual aptamers from SELEX pool 4520 NapdU and 4531 TrpdU using purified SpA protein serially diluted from 0.001-100 nmol l$^{-1}$ (FIG. 4A) and whole cells diluted to 10$^7$, 10$^6$, 10$^5$, and 10$^4$ CFU ml$^{-1}$ (FIG. 4B).
Figure 4A:
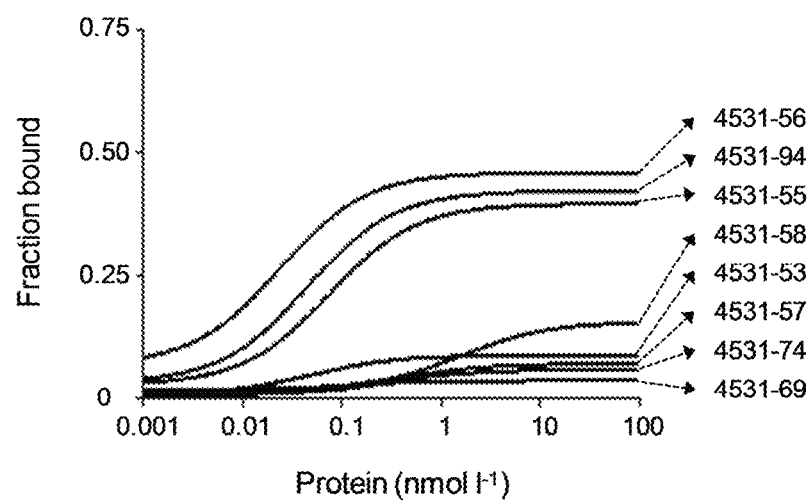
Figure 4B:
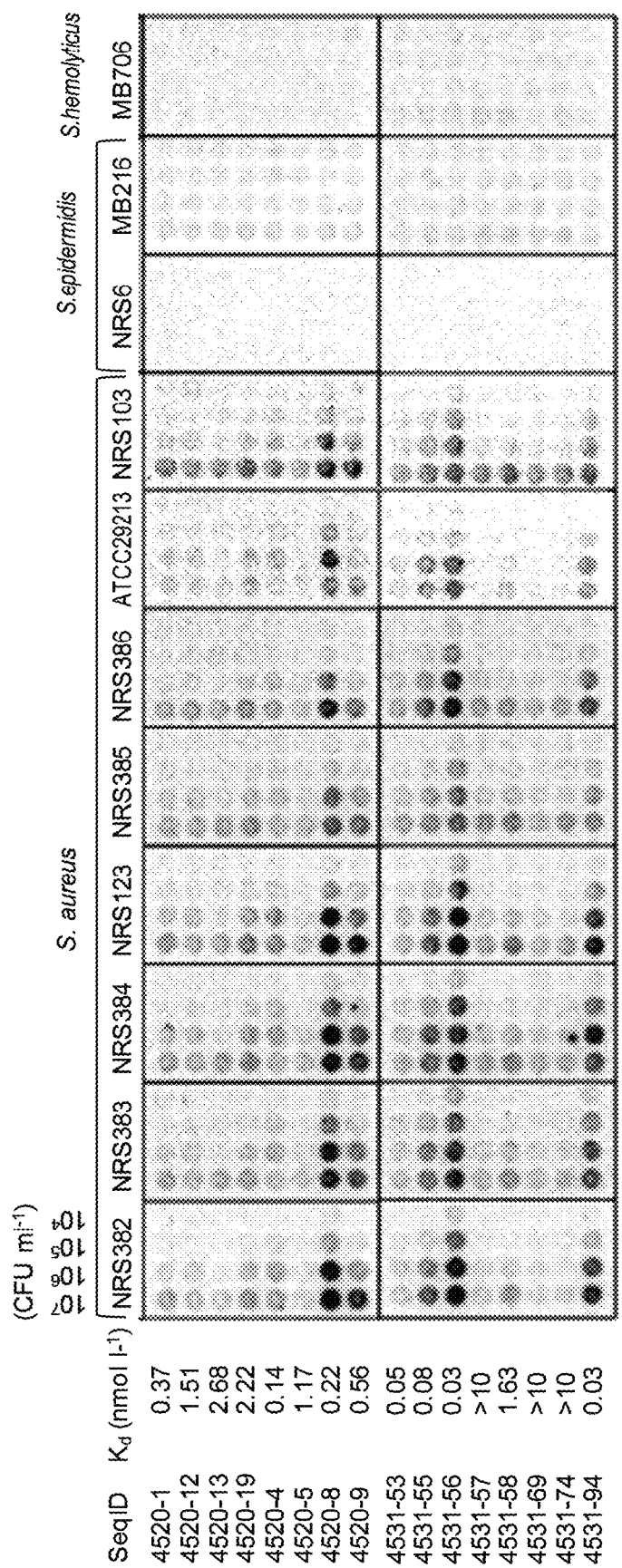

Aptamer binding affinities to purified *S. aureus* proteins correlated well with the observed binding to whole bacteria. Two of the SpA-NapdU clones (4520-8 and 4520-9) and three of the SpA-TrpdU clones (4531-55, 4531-56, 4531-94) were able to bind whole cells of all *S. aureus* strains tested, with a detection limit of ~10$^4$ cells per well (10$^5$-10$^6$ cells ml$^{-1}$) in a radiolabel filter binding assay. Binding to *S. epidermidis* or *S. haemolyticus* cells was not observed, indicating good specificity of these aptamers (see FIG. 4B). Similar binding characteristics were observed for the ClfA and ClfB aptamers. In contrast, most of the FnbA and FnbB aptamers that strongly bound to *S. aureus* also had some affinity to *S. epidermidis* and *S. haemolyticus*. aptamers directed to the Isd proteins, in particular IsdC, showed strong and specific binding to *S. aureus* cells, and signals were enhanced when the bacteria had been grown under iron-limiting conditions. SasD aptamers failed to bind whole cells, although it is not clear whether this is due to the rather modest affinity or due to low expression levels of this surface protein Capture of *S. aureus* Cells with Cell Surface Protein Directed Aptamers Biotinylated aptamers were prepared enzymatically via primer extension, using PBDC primers (5'photocleavable biotin, D-spacer and cy3). For immobilization, 1 pmol of PBDC aptamers were added to 20 µl MyOne Streptavidin C1 beads (10 mg ml$^{-1}$), and shaken for 15 min, resulting in ~90% efficiency of immobilization based on cy3 measurements in the non-captured supernatant fraction. Bacteria were grown for 16 hours at 35° C. in LB broth cultures or on tryptic soy agar with 5% sheep blood and 0.1 mmol l$^{-1}$ dipyridyl to create iron-limiting conditions. Cell suspensions containing up to 10$^6$ bacteria in 50 µl SB18T were added to the capture beads. After incubation with shaking for 1 h at 37° C., the beads were washed and resuspended in 50 µl SB18T. Cells in the non-captured supernatant, wash fraction, and on the beads were enumerated by quantitative plating of serial dilutions onto LB agar. Capture efficiency via quantitative culture was also determined in mixed populations and over a range of cell densities (10$^1$-10$^7$ CFU ml$^{-1}$).

Figure 1B:
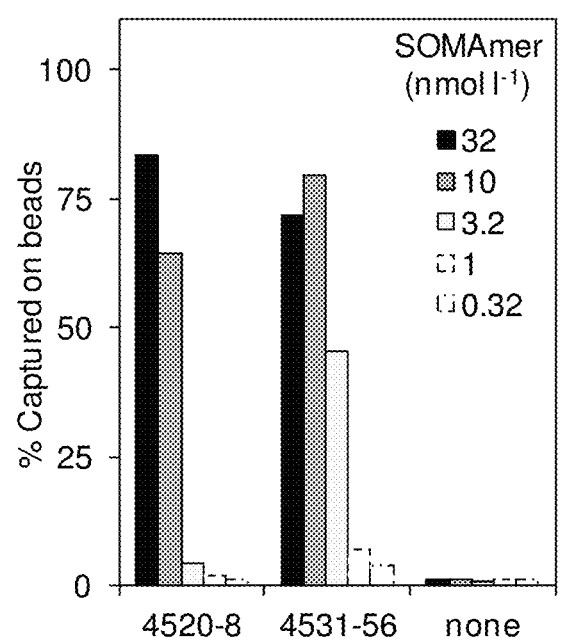
Figure 5A:
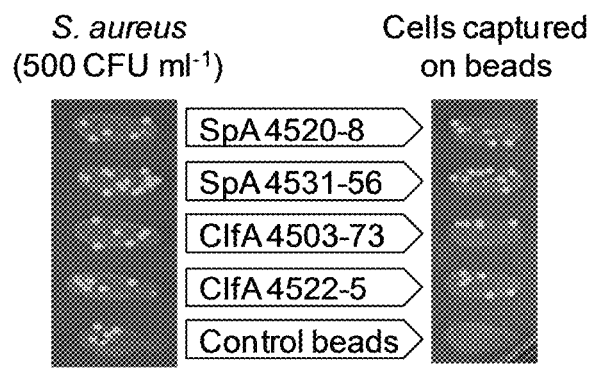
FIGS. 5A-B show the capture of bacterial cells with SpA and ClfA aptamers immobilized on paramagnetic streptavidin beads. Efficiency of capture was monitored by semi-quantitative culture at low cell density (FIG. 5A) or by decrease in turbidity at high cell density (FIG. 5B).
Figure 5B:
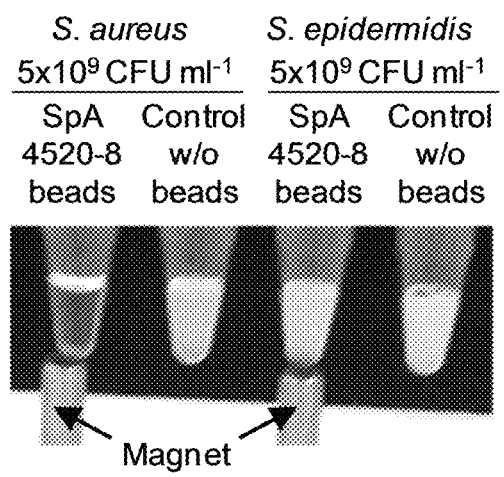

The number of target molecules per cell is unknown for any of these surface proteins and expression levels may vary depending on growth conditions and growth phase. However, assuming 1000 copies per cell and using 10$^7$ CFU ml$^{-1}$ would represent a target concentration of 20 pmol l$^{-1}$, which is at or below the typical aptamer K$_d$'s. Thus, the radiolabel filter binding assays, where the aptamers are present at low concentrations of 10-20 pmol l$^{-1}$, is limited to relatively high cell densities. To drive the binding reaction, we used higher concentrations (20 nmol l$^{-1}$) of biotinylated SpA aptamers as capture agents attached to beads, and were able to detect as few as 50 cells in a 0.1 mL sample (FIG. 1A). Aptamer concentrations of 10 nmol l$^{-1}$ or above were required for efficient capture of *S. aureus* at such low cell densities (FIG. 1B). Aptamers were able to bind selectively to *S. aureus* cells in mixed cultures that contained *S. aureus*, *S. epidermidis*, and *E. coli* each at 10$^5$-10$^6$ CFU ml$^{-1}$. The best performing binding agents were SpA 4520-8 and ClfA 4503-73, demonstrating low non-specific binding comparable to random sequence modified aptamer controls. Capture of *S. aureus* on paramagnetic aptamer beads was efficient over a wide range of cell densities, from 5×10$^2$ to 5×10$^9$ CFU ml$^{-1}$ (FIG. 5).

Example 3: Enhanced Detection of *S. aureus* Using Aptamer-Based Enrichment

This example provides exemplary methods for enhancing the detection of a microorganism (e.g., *S. aureus*) in a sample by enriching the microorganism in the sample by aptamer based capture followed by a subsequent detection method (e.g., PCR).

Capture of *S. aureus* cells was also achieved with 25 nmol l$^{-1}$ of synthetic, biotinylated aptamers (50 mers) attached to paramagnetic SA beads (15 min, 37° C., with intermittent shaking). The beads were washed twice with 100 µl of SB18 to remove any unbound cells, and resuspended in 50 µl SB18. Full-length, amplifiable aptamers were added (50 µl of 20 nmol l$^{-1}$), and the beads were incubated for 15 min at 37° C. with intermittent shaking to allow coating of the cells with these surface component specific aptamers. After washing five times for 2 min each with 100 µl of SB18/1 mmol l$^{-1}$ dextran sulfate/0.01% Tween-20 and twice with 100 µl of SB18, bound aptamers were eluted, cleaned up on primer capture beads, and used for qPCR with primers specific for the 5' and 3' fixed regions as described (Gold et al., 2010).

Figure 2:
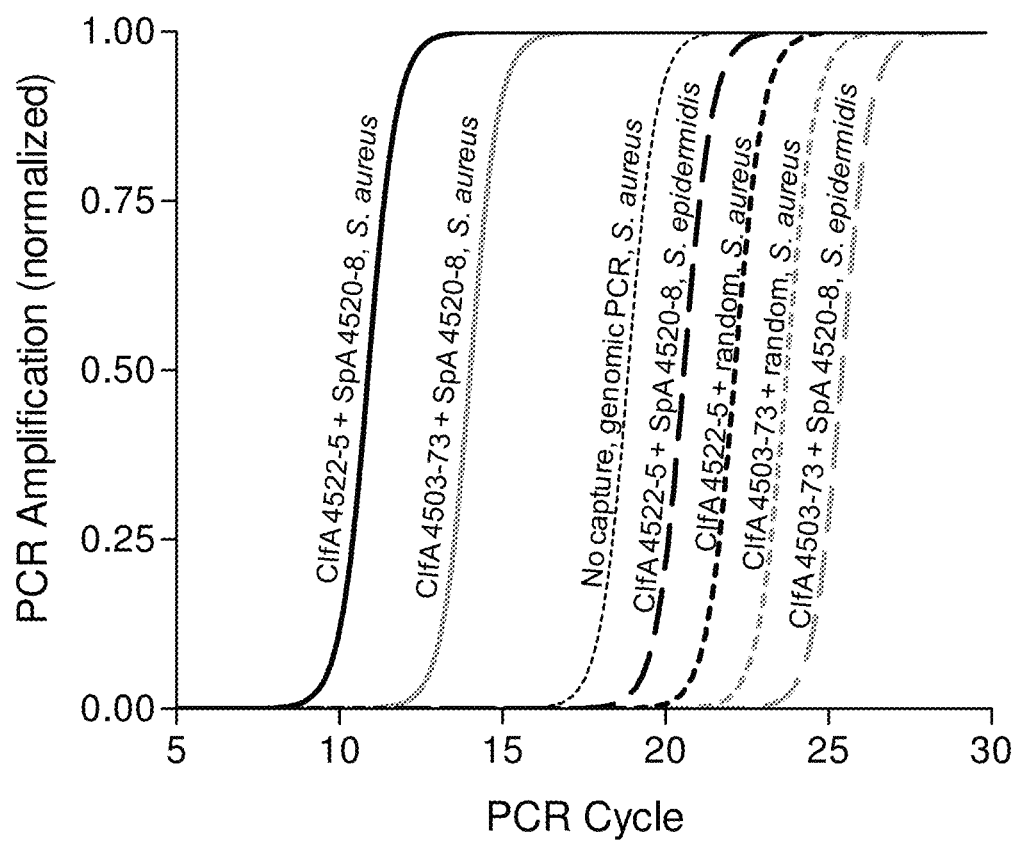
FIG. 2 shows aptamer-based capture of *Staphylococcus aureus*, and signal amplification via qPCR of aptamers bound to highly abundant cell surface components compared to qPCR of single genomic copies. Non-amplifiable, biotinylated ClfA aptamers 4522-5 or 4503-73 were used for capture of *S. aureus* or *S. epidermidis* (negative control, followed by detection with amplifiable SpA aptamer 4520-8. Random aptamer library was used as negative control for detection. PCR amplification of a genomic target (sasD gene) was performed for reference, using the same cell titer (10$^8$ cells ml$^{-1}$).

Capture of *S. aureus* cells proved useful for downstream detection by PCR, either for enrichment of the sample when cell densities were low, or to remove PCR inhibitors. Coating of the *S. aureus* cell surface with full-length, amplifiable aptamers allowed the faster detection by qPCR of the aptamers compared to qPCR of a genomic target, since each cell contained hundreds of copies of the target surface component for detection, compared to a single genome. In the example shown in FIG. 2, *S. aureus* cells were captured with non-amplifiable ClfA aptamers and coated with amplifiable SpA aptamers or random sequence aptamers controls, followed by qPCR using aptamers-specific primers. Separately, the cells were lysed and subjected to qPCR using *S. aureus* specific genomic primers, which was clearly less efficient compared to qPCR of bound aptamers. An shift by up to eight cycles in qPCR detection was observed, from 10 cycles for aptamers qPCR to 18 cycles for genomic qPCR, which is consistent with a ratio of several hundred copies (2$^8$=256) of surface-bound aptamers to only a single genome. The method of ClfA aptamer capture and SpA aptamer detection was specific for *S. aureus* cells, since *S. epidermidis* cells that do not possess ClfA or SpA did not result in any aptamer amplification above background. Capture of bacteria on beads followed by detection with aptamers not only enabled enrichment from low cell density suspensions, but also allowed the efficient removal of PCR inhibitors. Direct genomic PCR failed when cells were in matrices containing excess salt (e.g., 1 mol l$^{-1}$ NaCl or 0.5 mol l$^{-1}$ KCl) or low levels of solvents (e.g., 5% isopropanol), unless the cells were captured first to remove these known PCR inhibitors (Abu Al-Soud and Radstrom, 1998; Schrader et al., 2012).

REFERENCES

Abu Al-Soud, W. and Radstrom, P. (1998) Capacity of nine thermostable DNA polymerases to mediate DNA amplification in the presence of PCR-inhibiting samples. *Appl Environ Microbiol* 64, 3748-3753.

Cao, X., Li, S., Chen, L., Ding, H., Xu, H., Huang, Y., Li, J., Liu, N. et al. (2009) Combining use of a panel of ssDNA aptamers in the detection of *Staphylococcus aureus*. *Nucleic Acids Res* 37, 4621-4628.

Dreisbach, A., van Dijl, J. M. and Buist, G. (2011) The cell surface proteome of *Staphylococcus aureus*. *Proteomics* 11, 3154-3168.

Dwivedi, H. P., Smiley, R. D. and Jaykus, L. A. (2013) Selection of DNA aptamers for capture and detection of *Salmonella typhimurium* using a whole-cell SELEX approach in conjunction with cell sorting. *Appl Microbiol Biotechnol* 97, 3677-3686.

Falugi, F., Kim, H. K., Missiakas, D. M. and Schneewind, O. (2013) Role of protein A in the evasion of host adaptive immune responses by *Staphylococcus aureus*. *MBio* 4, e00575-00513.

Gill, S. R., Fouts, D. E., Archer, G. L., Mongodin, E. F., Deboy, R. T., Ravel, J., Paulsen, I. T., Kolonay, J. F. et al. (2005) Insights on evolution of virulence and resistance from the complete genome analysis of an early methicillin-resistant *Staphylococcus aureus* strain and a biofilm-producing methicillin-resistant *Staphylococcus epidermidis* strain. *J Bacteriol* 187, 2426-2438.

Gold, L., Ayers, D., Bertino, J., Bock, C., Bock, A., Brody, E. N., Carter, J., Dalby, A. B. et al. (2010) Aptamer-based multiplexed proteomic technology for biomarker discovery. *PLoS One* 5, e15004.

Gold, L., Walker, J. J., Wilcox, S. K. and Williams, S. (2012) Advances in human proteomics at high scale with the SOMAscan proteomics platform. *N Biotechnol* 29, 543-549.

Grigg, J. C., Ukpabi, G., Gaudin, C. F. and Murphy, M. E. (2010) Structural biology of heme binding in the *Staphylococcus aureus* Isd system. *J Inorg Biochem* 104, 341-348.

Hussain, M., Becker, K., von Eiff, C., Schrenzel, J., Peters, G. and Herrmann, M. (2001) Identification and characterization of a novel 38.5-kilodalton cell surface protein of *Staphylococcus aureus* with extended-spectrum binding activity for extracellular matrix and plasma proteins. *J Bacteriol* 183, 6778-6786.

Kobayashi, S. D., and Deleo, F. R. (2013) *Staphylococcus aureus* Protein A Promotes Immune Suppression. *MBio* 4, e00764-13. doi:10.1128

Marraffini, L. A., Dedent, A. C. and Schneewind, 0. (2006) Sortases and the art of anchoring proteins to the envelopes of gram-positive bacteria. *Microbiol Mol Biol Rev* 70, 192-221.

Mazmanian, S. K., Skaar, E. P., Gaspar, A. H., Humayun, M., Gornicki, P., Jelenska, J., Joachmiak, A., Missiakas, D. M. and Schneewind, O. (2003) Passage of heme-iron across the envelope of *Staphylococcus aureus*. *Science* 299, 906-909.

McCarthy, A. J. and Lindsay, J. A. (2010) Genetic variation in *Staphylococcus aureus* surface and immune evasion genes is lineage associated: implications for vaccine design and host-pathogen interactions. *BMC Microbiol* 10, 173.

McDevitt, D., Nanavaty, T., House-Pompeo, K., Bell, E., Turner, N., McIntire, L., Foster, T. and Hook, M. (1997) Characterization of the interaction between the *Staphylococcus aureus* clumping factor (ClfA) and fibrinogen. *Eur J Biochem* 247, 416-424.

Ni Eidhin, D., Perkins, S., Francois, P., Vaudaux, P., Hook, M. and Foster, T. J. (1998) Clumping factor B (ClfB), a new surface-located fibrinogen-binding adhesin of *Staphylococcus aureus*. *Mol Microbiol* 30, 245-257.

Ochsner, U. A., Katilius, E. and Janjic, N. (2013) Detection of *Clostridium difficile* toxins A, B and binary toxin with slow off-rate modified aptamers. *Diagn Microbiol Infect Dis.* 76, 278-285.

Palma, M., Wade, D., Flock, M. and Flock, J. I. (1998) Multiple binding sites in the interaction between an extracellular fibrinogen-binding protein from *Staphylococcus aureus* and fibrinogen. *J Biol Chem* 273, 13177-13181.

Rao, S. S., Mohan, K. V., Gao, Y. and Atreya, C. D. (2013) Identification and evaluation of a novel peptide binding to the cell surface of *Staphylococcus aureus*. *Microbiol Res* 168, 106-112.

Roche, F. M., Massey, R., Peacock, S. J., Day, N. P., Visai, L., Speziale, P., Lam, A., Pallen, M. and Foster, T. J. (2003) Characterization of novel LPXTG-containing proteins of *Staphylococcus aureus* identified from genome sequences. *Microbiology* 149, 643-654.

Roche, F. M., Downer, R., Keane, F., Speziale, P., Park, P. W. and Foster, T. J. (2004) The N-terminal A domain of fibronectin-binding proteins A and B promotes adhesion of *Staphylococcus aureus* to elastin. *J Biol Chem* 279, 38433-38440.

Schneewind, O., Fowler, A. and Faull, K. F. (1995) Structure of the cell wall anchor of surface proteins in *Staphylococcus aureus*. *Science* 268, 103-106.

Schrader, C., Schielke, A., Ellerbroek, L. and Johne, R. (2012) PCR inhibitors—occurrence, properties and removal. *J Appl Microbiol* 113, 1014-1026.

Sorum, M., Sangvik, M., Stegger, M., Olsen, R. S., Johannessen, M., Skov, R. and Sollid, J. U. (2013) *Staphylococcus aureus* mutants lacking cell wall-bound protein A found in isolates from bacteraemia, MRSA infection and a healthy nasal carrier. *Pathog Dis* 67, 19-24.

Speziale, P., Pietrocola, G., Rindi, S., Provenzano, M., Provenza, G., Di Poto, A., Visai, L. and Arciola, C. R. (2009) Structural and functional role of *Staphylococcus aureus* surface components recognizing adhesive matrix molecules of the host. *Future Microbiol* 4, 1337-1352.

Stranger-Jones, Y. K., Bae, T. and Schneewind, O. (2006) Vaccine assembly from surface proteins of *Staphylococcus aureus*. *Proc Natl Acad Sci USA* 103, 16942-16947.

Timofeyeva, Y., Scully, I. L. and Anderson, A. S. (2014) Immunofluorescence microscopy for the detection of surface antigens in methicillin-resistant *Staphylococcus aureus* (MRSA). *Methods Mol Biol* 1085, 85-95.

Vaught, J. D., Bock, C., Carter, J., Fitzwater, T., Otis, M., Schneider, D., Rolando, J., Waugh, S. et al. (2010) Expanding the chemistry of DNA for in vitro selection. *J Am Chem Soc* 132, 4141-4151.

Ythier, M., Resch, G., Waridel, P., Panchaud, A., Gfeller, A., Majcherczyk, P., Quadroni, M., and Moreillon, P. (2012) Proteomic and transcriptomic profiling of *Staphylococcus aureus* surface LPXTG-proteins: correlation with agr genotypes and adherence phenotypes. *Mol Cell Proteomics* 11, 1123-1139.

The invention claimed is:

1. A nucleic acid molecule comprising the sequence of SEQ ID NOs: 10-12, wherein n is independently, for each occurrence, a C-5 modified pyrimidine selected from the group consisting of 5-(N-benzylcarboxyamide)-2'-deoxycytidine (BndC); 5-(N-2-phenylethylcarboxyamide-2'-deoxycytidine (PEdC); 5-(N-3-phenylpropylcarboxyamide)-2'-deoxycytidine (PPdC); 5-(N-1-naphthylmethylcarboxyamide-2'-deoxycytidine (NapdC); 5-(N-2-naphthylmethyl-carboxyamide)-2'-deoxycytidine (2NapdC); 5-(N-1-naphthyl-2-ethylcarboxyamide)-2'-deoxycytidine (NEdC); 5-(N-2-naphthyl-2-naphthyl-2-ethylcarboxyamide)-2'-deoxycytidine (2NEdC); 5-(N-benzylcarboxyamide)-2'-deoxyuridine (BndU); 5-(N-isobutylcarboxyamide-2'-deoxyuridine (iBudU); 5-(N-tryptaminocarboxyamide-2'-deoxyuridine (TrpdU); 5-(N-[1-(3-trimethylamonium) propyl]carboxyamide)-2'-deoxyuridine chloride and 5-(N-naphthylmethylcarboxyamide)-2'-deoxyuridine (NapdU), wherein the nucleic acid molecule is from about 40 to about 100 nucleotides in length.

2. The nucleic acid molecule of claim 1, wherein C-5 modified pyrimidine is a 5-(N-benzylcarboxyamide)-2'-deoxyuridine (BndU).

3. The nucleic acid molecule of claim 1, wherein the nucleic acid molecule has affinity for a ClfA protein.

4. A kit for detecting the presence or absence of a microorganism in a sample comprising a nucleic acid molecule of claim 1.

* * * * *